United States Patent
Zhang

(10) Patent No.: US 10,281,384 B2
(45) Date of Patent: *May 7, 2019

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 252 days.

This patent is subject to a terminal disclaimer.

(21) Appl. No.: 15/224,111

(22) Filed: Jul. 29, 2016

(65) Prior Publication Data

US 2017/0058748 A1 Mar. 2, 2017

Related U.S. Application Data

(63) Continuation-in-part of application No. 15/062,449, filed on Mar. 7, 2016, which is a continuation-in-part
(Continued)

(51) Int. Cl.
*G01N 15/00* (2006.01)
*G01N 15/06* (2006.01)
*F01N 13/00* (2010.01)

(52) U.S. Cl.
CPC ..... *G01N 15/0656* (2013.01); *B01D 2273/18* (2013.01); *F01N 13/008* (2013.01);
(Continued)

(58) Field of Classification Search
CPC ........... G01N 15/0656; G01N 15/0606; G01N 2015/0046; B01D 2273/18; F01N 13/008; F01N 2560/05
See application file for complete search history.

(56) References Cited

U.S. PATENT DOCUMENTS 4,091,835 A * 5/1978 Frampton .............. G05D 7/012
137/499
7,739,898 B2 6/2010 Shaddock et al.
(Continued)

OTHER PUBLICATIONS

Bilby, David, "Method and System for Exhaust Particulate Matter Sensing," U.S. Appl. No. 14/937,632, filed Nov. 10, 2015, 48 pages.
(Continued)

*Primary Examiner* — Blake A Tankersley
(74) *Attorney, Agent, or Firm* — Julia Voutyras; McCoy Russell LLP

(57) ABSTRACT

Methods and systems are provided sensing particulate matter by a particulate matter sensor positioned downstream of a diesel particulate filter in an exhaust system. In one example, a method may include increasing an inlet opening of the particulate matter sensor when an exhaust flow rate falls below a threshold to allow more particulates to enter the particulate matter sensor and further includes decreasing the inlet opening when the exhaust flow rate rises above the threshold to reduce the particulates entering the sensor. By adjusting the amount of particulates entering the sensor based on the exhaust rate, and further including a plurality of flow redirectors inside the sensor, the rate of deposition of the sensor and hence the sensitivity of the sensor to the exhaust flow rate may be maintained at a desired level, and independent of the exhaust flow rate.

17 Claims, 10 Drawing Sheets

Related U.S. Application Data of application No. 14/835,270, filed on Aug. 25, 2015.

(52) U.S. Cl.
CPC ...... *F01N 2240/20* (2013.01); *F01N 2560/05* (2013.01); *G01N 2015/0046* (2013.01)

(56) References Cited

U.S. PATENT DOCUMENTS

| | | |
|---|---|---|
| 8,225,648 B2 | 7/2012 | Nelson |
| 2003/0234378 A1 | 12/2003 | Hartly et al. |
| 2005/0262817 A1* | 12/2005 | Hatanaka .............. F01N 3/0212 55/282.3 |
| 2008/0087012 A1* | 4/2008 | Konstandopoulos ........................ F01N 3/0222 60/311 |
| 2012/0125081 A1* | 5/2012 | Yadav .................... F01N 11/00 73/23.33 |
| 2015/0267649 A1 | 9/2015 | Remes |
| 2015/0355066 A1 | 12/2015 | Zhang |

OTHER PUBLICATIONS

Zhang, Xiaogang, "System for Sensing Particulate Matter," U.S. Appl. No. 14/966,408, filed Dec. 11, 2015, 40 pages.

Zhang, Xiaogang, "Method and System for Exhaust Particulate Matter Sensing," U.S. Appl. No. 15/187,149, filed Jun. 20, 2016, 83 pages.

\* cited by examiner

METHOD AND SYSTEM FOR EXHAUST PARTICULATE MATTER SENSING

CROSS REFERENCE TO RELATED APPLICATIONS

The present application is a continuation-in-part of U.S. patent application Ser. No. 15/062,449, entitled "METHOD AND SYSTEM FOR EXHAUST PARTICULATE MATTER SENSING," filed on Mar. 7, 2016, which is a continuation-in-part of U.S. patent application Ser. No. 14/835,270, entitled "METHOD AND SYSTEM FOR EXHAUST PARTICULATE MATTER SENSING," filed on Aug. 25, 2015, the entire contents of each of which are hereby incorporated by reference for all purposes.

FIELD

The present description relates generally to the design and use of resistive-type particle matter (PM) sensors in an exhaust gas flow.

BACKGROUND/SUMMARY

Diesel combustion exhaust is a regulated emission. Diesel particulate matter (PM), is the particulate component of diesel exhaust, which includes diesel soot and aerosols such as ash particulates, metallic abrasion particles, sulfates, and silicates. When released into the atmosphere, PMs can take the form of individual particles or chain aggregates, with most in the invisible sub-micrometer range of 100 nanometers. Various technologies have been developed for identifying and filtering out exhaust PMs before the exhaust is released to the atmosphere.

As an example, soot sensors, also known as PM sensors, may be used in vehicles having internal combustion engines. A PM sensor may be located upstream and/or downstream of a diesel particulate filter (DPF), and may be used to sense PM loading on the filter and diagnose operation of the DPF. Typically, the PM sensor may sense a particulate matter or soot load based on a correlation between a measured change in electrical conductivity (or resistivity) between a pair of electrodes placed on a planar substrate surface of the sensor with the amount of PM deposited between the measuring electrodes. Specifically, the measured conductivity provides a measure of soot accumulation. As such, the sensitivity of the PM sensors to measure PM in the exhaust may depend on the exhaust flow rate, with increased exhaust flow rate leading to increased PM sensor sensitivity and decreased exhaust flow rate resulting in decreased PM sensor sensitivity. With this increased dependence on exhaust flow rate, the PM sensor capturing the PMs exiting the DPF, may not truly reflect the DPF filtering capabilities. Furthermore, PM sensors may be prone to contamination from impingement of water droplets and/or larger particulates present in the exhaust gases, thus affecting the PM sensor sensitivity and leading to errors in the output of the PM sensor.

One example PM sensor design is shown by Nelson in U.S. Pat. No. 8,225,648B2. Therein, a PM sensor includes a flow redirector and a barrier positioned around a PM sensor element to filter out the larger particulates from impinging the PM sensor element. The barrier thus serves to block larger particulates in the exhaust flow from impinging on the PM sensor element, thereby reducing PM sensor sensitivity fluctuations due to large particulates depositing on the PM sensor element.

However, the inventors herein have recognized potential issues with such an approach. As one example, the PM sensor sensitivity may continue to depend on the incoming exhaust flow rate. In one example, the issues described above may be partly addressed by a method for adjusting an amount of opening of an inlet to a particulate matter sensor positioned in an exhaust flow in response to an exhaust flow rate of the exhaust flow upstream of the particulate matter sensor, and flowing exhaust past a plurality of flow plates towards a particulate matter sensor element positioned proximate to the plurality of flow plates. The plurality of flow plates may be positioned proximate to a sensor element. Larger particulates may be blocked at the plates when exhaust flows through the plurality of flow plates, and additionally, smaller soot particulates may be directed towards the sensor element and uniformly distributed across the electrodes of the sensor element. In addition, by adjusting the amount of inlet opening based on exhaust flow rate, the amount of particulates entering and thus being deposited across a sensor element positioned within may be controlled. In this way, the sensitivity of the particulate matter sensor may become independent of the exhaust flow rate and the PM sensor output may begin to measure the DPF filtering capabilities more accurately and reliably.

As one example, when the exhaust flow rate falls below a threshold, the amount of opening of the inlet of the PM sensor may be increased to allow more exhaust gas into the PM sensor for subsequent deposition on a PM sensor element positioned inside the PM sensor. When the exhaust flow rate rises above the threshold, the amount of inlet opening may be decreased to reduce the exhaust gas entering the PM sensor. Herein, the increasing and the decreasing of the amount of inlet opening may be regulated by adjusting (e.g., rotating) a movable flow controller positioned at the inlet. In this way, the amount of exhaust gas and thereby the amount of particulates getting deposited on the PM sensor element positioned proximate to an outlet of the PM sensor may become independent of the incoming exhaust flow rate, thereby measuring PMs exiting the DPF more accurately and reliably. Further, larger particulates and/or water droplets may be trapped by the first flow redirector and the plurality of flow plates positioned inside the PM sensor. Therefore, the PM sensor element may be protected from impingement of water droplets and larger particulates. Overall, these characteristics of the sensor may cause an output of the PM sensor to be more accurate, thereby increasing the accuracy of estimating particulate loading on a particulate filter.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
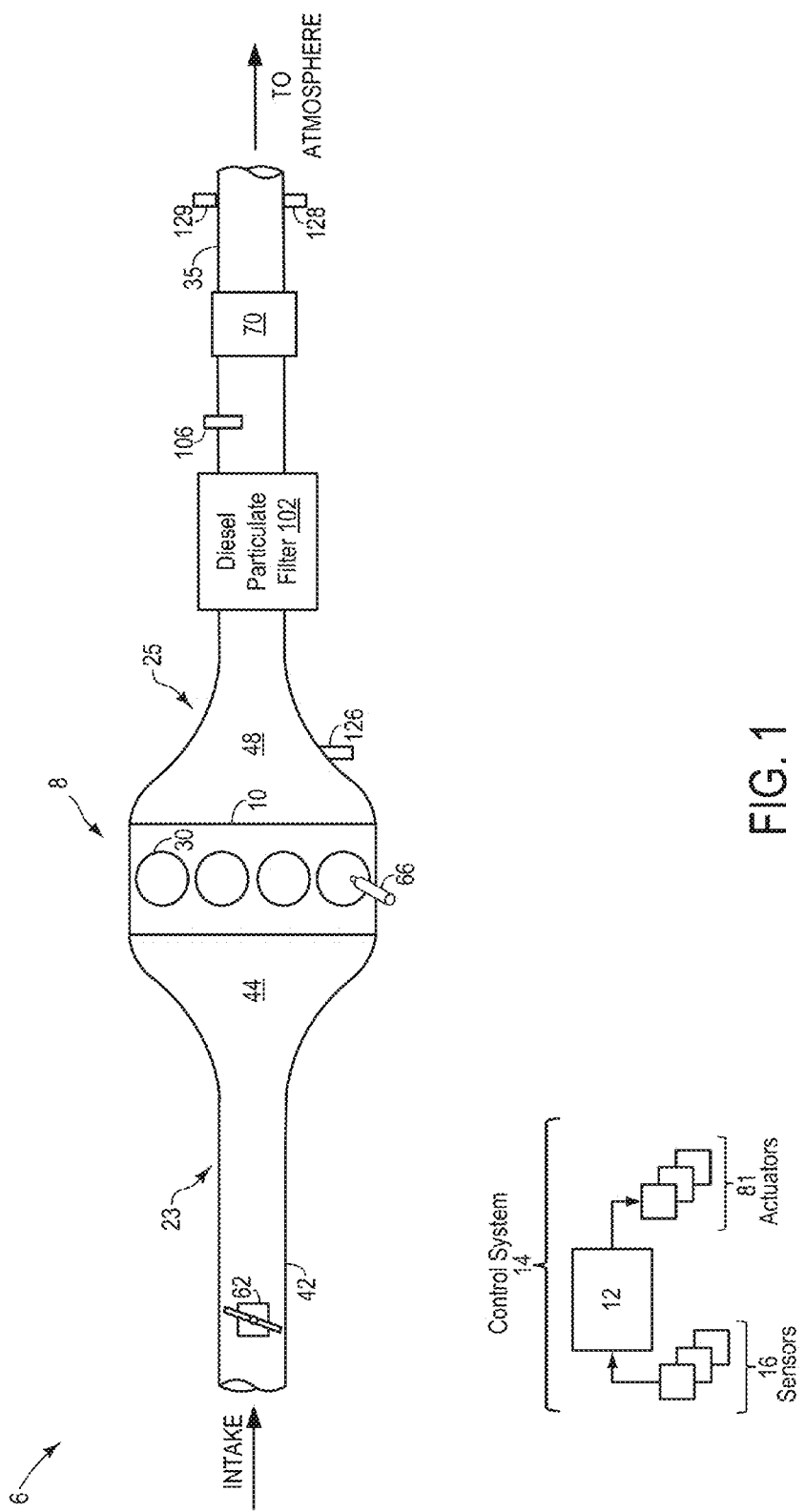
FIG. 1 shows a schematic diagram of an engine and an associated particulate matter (PM) sensor positioned in an exhaust flow.
Figure 2A:
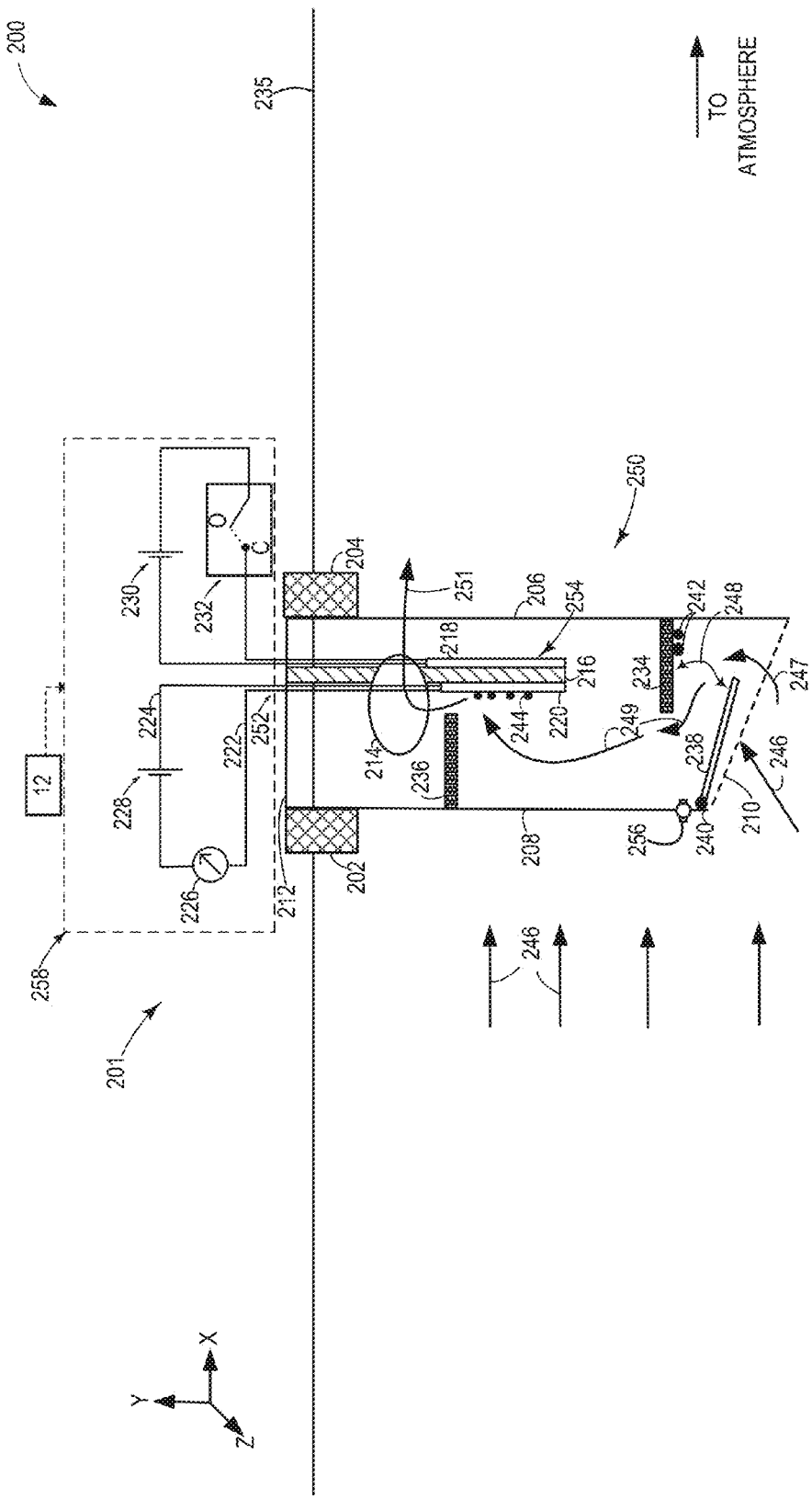
FIGS. 2A-2B show magnified views of the PM sensor wherein an inlet opening is increased or decreased based on an exhaust flow rate.
Figure 2B:
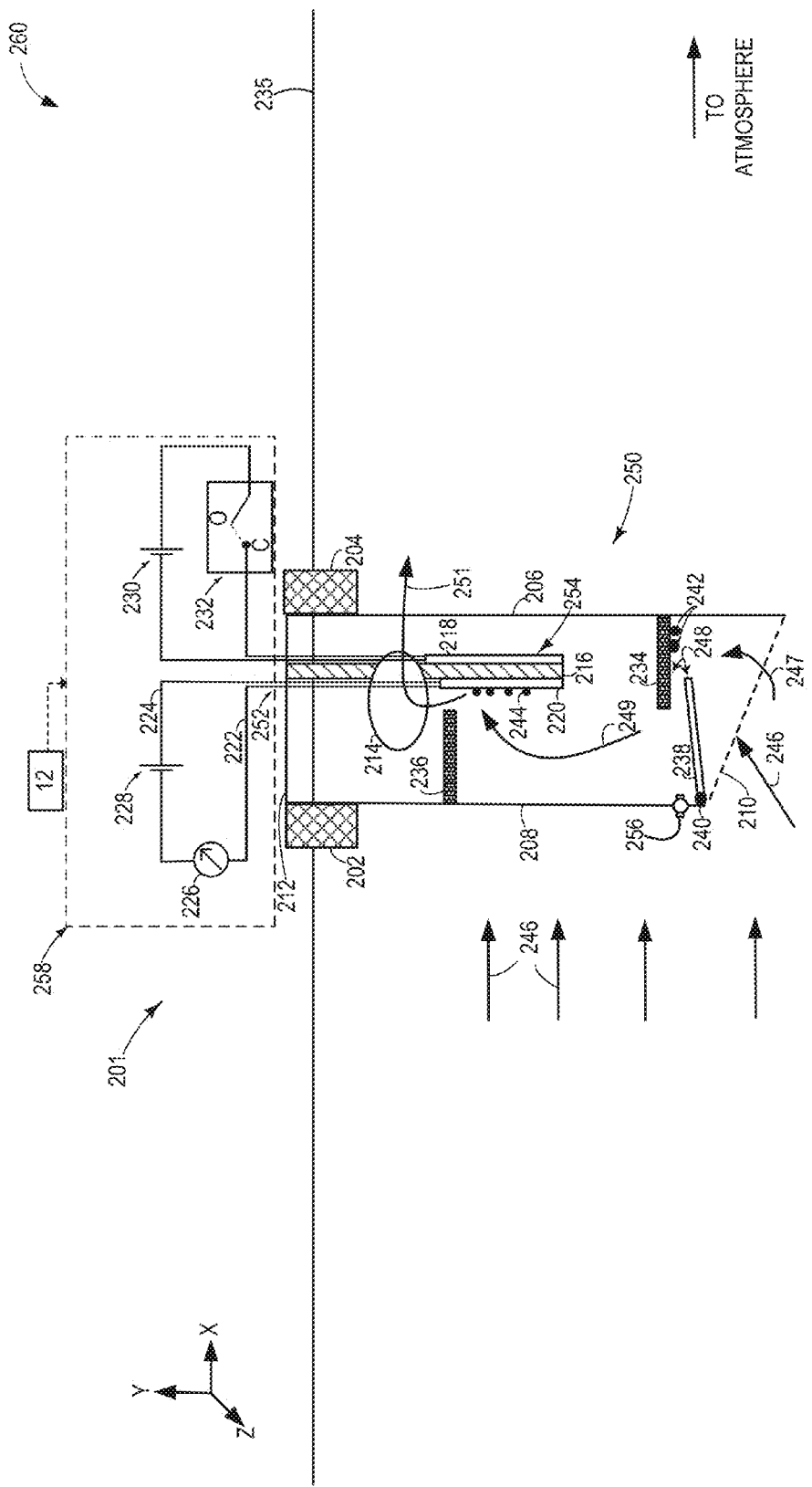
Figure 2C:
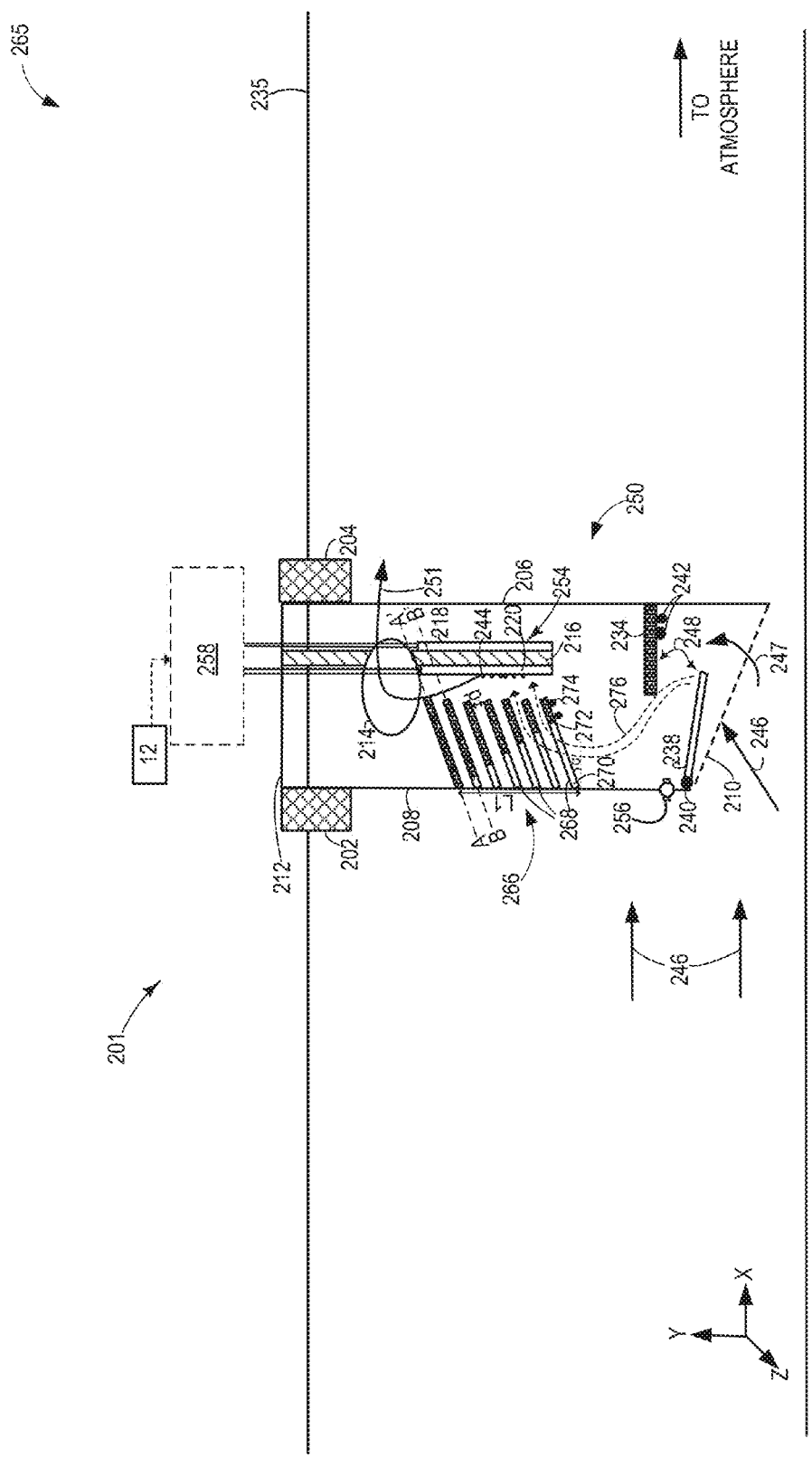
FIG. 2C shows an example embodiment of the PM sensor having a plurality of parallel flow plates positioned proximate to an outlet of the PM sensor.

The following description relates to sensing particulate matter (PM) in an exhaust flow of an engine system, such as the engine system shown in FIG. 1. A PM sensor placed in an exhaust passage of the engine system may include a flow controller and a first flow redirector positioned proximate to an inlet of the PM sensor. An inlet opening of the PM sensor may be adjusted based on the exhaust flow rate by rotating the flow controller of the PM sensor, as shown in FIGS. 2A and 2B. In a first example embodiment, the PM sensor may include a plurality of parallel flow plates separated by a space and stacked between the inlet and an outlet of the PM sensor as shown in FIG. 2C. The plurality of flow plates may be semi-circular discs coupled to a side surface of the PM sensor, having openings (as shown in cross-sectional views of FIGS. 2C and 2D) that are configured to direct exhaust towards a sensor element of the PM sensor. In a second example embodiment, the plurality of flow plates may be angled with respect to each other and interlaid between the inlet opening and the sensor element as shown in FIG. 2F. A controller may be configured to perform a control routine, such as the routine of FIG. 3 to adjust an amount of opening of the inlet opening of the PM sensor based on the exhaust flow rate. In addition, the controller may intermittently clean the PM sensor (as shown in the method presented at FIG. 4) to enable continued PM detection and perform diagnostics on a particulate filter positioned upstream of the PM sensor based on an output of the PM sensor (as shown in the method presented at FIG. 5). An example relation between the PM sensor inlet opening and the PM sensor loading based on the exhaust flow rate is depicted with reference to FIG. 6. In this way, by adjusting the inlet opening based on the exhaust flow rate, the PM sensor sensitivity may become independent of the incoming exhaust flow rate. Further, larger particulates and/or water droplets may be trapped by the flow redirector and the plurality of flow plates. Therefore, the PM sensor element may be protected from impingement of water droplets and larger particulates. Overall, the functioning of the PM sensor to estimate the filtering capabilities of the DPF (and thereby to detect DPF leaks) may be improved and exhaust emissions compliance may be improved as PMs in the exhaust may be detected more accurately and reliably.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PMs, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIG. 2, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), a motor actuator controlling PM sensor opening (e.g., controller opening of a valve or plate in an inlet of the PM sensor), etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. Example routines are described herein with reference to FIGS. 3-5.

Turning now to FIGS. 2A-2B, schematic views of a first example embodiment of a particulate matter (PM) sensor 201 (such as PM sensor 106 of FIG. 1) is shown. FIG. 2A shows a first schematic 200 of the PM sensor 201 with a flow controller 238 in a first configuration and FIG. 2B shows a second schematic 260 of the PM sensor 201 with the flow controller 238 in a second configuration. The PM sensor 201 may be configured to measure PM mass and/or concentration in the exhaust gas, and as such, may be coupled to an exhaust passage (e.g., such as the exhaust passage 35 shown in FIG. 1), upstream or downstream of a diesel particulate filter (such as DPF 102 shown in FIG. 1).

As shown in FIGS. 2A-2B, the PM sensor 106 is disposed inside exhaust passage 235 with exhaust gases flowing from downstream of a diesel particulate filter towards an exhaust tailpipe, as indicated by arrows 246. PM sensor 106 includes a protection tube 250 that may serve to protect a PM sensor element 254 of the PM sensor 201 housed within and may additionally serve to redirect exhaust gas flow over the PM sensor element 254 as explained below.

The PM sensor element 254 includes a pair of planar interdigitated electrodes 220 forming a "comb" structure. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes 220 are formed on a substrate 216 that is typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes. The spacing between the comb "tines" of the two electrodes may typically be in the range from 10 micrometers to 100 micrometers with the linewidth of each individual "tine" being about the same value, although the latter is not necessary. As shown in FIGS. 2A-2B, the interdigitated electrodes 220 extend along and cover a portion of the substrate 216.

A positive electrode of the pair of interdigitated electrodes 220 is connected with connecting wires 224 to a positive terminal of a voltage source 228 of an electric circuit 258. A negative electrode of the pair of interdigitated electrodes 220 is connected to a measurement device 226 via a connecting wire 222, and further connected to a negative terminal of the voltage source 228 of the electric circuit 258. The interconnecting wires 222 and 224, the voltage source 228 and the measurement device 226 are part of the electric circuit 258 and are housed outside the exhaust passage 35 (as one example, <1 meter away). Further, the voltage source 228 and the measurement device of the electric circuit 258 may be controlled by a controller, such as controller 12 of FIG. 1, so that particulate matter collected at the PM sensor may be used for diagnosing leaks in the DPF, for example. As such, the measurement device 226 may be any device capable of reading a resistance change across the electrodes, such as a voltmeter. As PM or soot particles get deposited between the electrodes 220, the resistance between the electrode pair may start to decrease, which is indicated by a decrease in the voltage measured by the measurement device 226. The controller 12 may be able to determine the resistance between the electrodes 220 as a function of voltage measured by the measurement device 226 and infer a corresponding PM or soot load on the planar electrodes 220 of the PM sensor 201. By monitoring the load on the PM sensor 201, the exhaust soot load downstream of the DPF may be determined, and thereby used to diagnose and monitor the health and functioning of the DPF.

The PM sensor element 254 also includes a heating element 218 that is be integrated into the sensor substrate 216. In alternate embodiments, the PM sensor element 254 may not include a heating element 218. The heating element 218 may comprise, but is not limited to, a temperature sensor, and a heater. Possible materials for the heater and the temperature sensor forming the heating element 218 may include platinum, gold, palladium, and the like; and alloys, oxides, and combinations comprising at least one of the foregoing materials, with platinum/alumina, platinum/palladium, platinum, and palladium. The heating element 218 may be used for regenerating the PM sensor element 254. Specifically, during conditions when the particulate matter load or soot load of the PM sensor element 254 is higher than a threshold, heating element 218 may be operated to burn accumulated soot particles from the surface of sensor. During PM sensor regeneration, the controller 12 may provide a voltage to a voltage source 230, which is needed for operating the heating element 218. In addition, the controller may close the switch 232 for a threshold time to apply the voltage via the voltage source 230 to the heating element 218 in order to raise the temperature of the heating element 218.

Subsequently, when the sensor electrodes are sufficiently clean, the controller may open the switch 232 to stop heating the heating element 218. By intermittently regenerating the PM sensor 201, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter. The sensitivity of the PM sensor may be affected by large particulates and/or water droplets getting deposited on the PM sensor element 254. In addition, the sensitivity of the PM sensor element 254 may further depend on the exhaust flow rate. Higher sensitivity is typically observed at higher exhaust flow, while lower sensitivity occurs at lower exhaust flow. It may be possible to filter out larger particulates and water droplets and obtain a flow independent PM sensor by using a design for the protection tube 250, as described below.

The protection tube 250 may be a hollow cylindrical tube with an upstream tube wall 208 (e.g., upstream facing wall), a downstream tube wall 206 (e.g., downstream facing wall), and a top surface 212. The upstream tube wall 208 may be closer to a DPF than the downstream tube wall 206 when positioned in an exhaust passage such as the exhaust passage 235 shown in FIG. 1 where the DPF is positioned upstream of the PM sensor. Further, exhaust gases flowing through the exhaust passage 135 may first contact the upstream tube wall 208 of the PM sensor. The top surface 212 may further include an inset portion 252 through which the PM sensor element 254 and its accompanying electrical connections may be inserted into the protection tube 250, and further be sealed to protect the PM sensor element 254 housed within the PM sensor 201. The protection tube 250 may be mounted onto the exhaust passage 35 via sensor boss 202 and 204 such that the central axis of the protection tube 250 is along the Y-axis, and also such that the central axis of the protection tube 250 is perpendicular to the exhaust passage 35 and the exhaust flow through the exhaust passage. As shown in FIGS. 2A-2B, the protection tube 250 extends into a portion of the exhaust passage 35. The depth to which the protection tube extends into the exhaust passage may depend on exhaust pipe diameter. In some examples, the protection tube may extend to about one third to two third of the exhaust pipe diameter. The bottom of the protection tube 250 may be cut at an angle (dashed line 210) forming an angled inlet that introduces exhaust flow into the PM sensor 201. Herein, the angled bottom portion (210) of the PM sensor

201 may be formed by cutting the protection tube 250 at a diagonal, for example a 30° or 45° angle with respect to the horizontal X-axis, as shown in FIG. 2A. As such, the length of the upstream tube wall 208 is smaller than the length of the downstream tube wall 206. Thus, the angled bottom potion 210 of the protection tube 250 serves as an inlet to the PM sensor 201, and henceforth referred to as inlet 210. The PM sensor 201 also includes an outlet 214 positioned a distance away from the inlet of the PM sensor 201. The outlet 214 may be a single hole or plurality of holes positioned along one or more of a back wall and a front wall of the protection tube 250 (not shown). As such, the front wall and the back surface of the protection tube 250 may be surfaces of the hollow cylindrical protection tube 250 that are different from the upstream tube wall 208 and the downstream tube wall 206. While the outlet 214 is shown as an elliptical hole in FIG. 2A, other shapes and sizes of the outlet 214 may also be used without departing from the scope of this disclosure.

The protection tube 250 further includes a first flow redirector 234 and a second flow redirector 236 mounted onto the inner wall (e.g., inside surface) of the hollow cylindrical protection tube 250. The first and the second flow redirectors, 234 and 236, may be made from portions of a circular plate and positioned on opposite sides of the interior of the protection tube 250 relative to the central axis of the protection tube 250. For example, the first flow redirector 234 may be mounted on the inner surface of the protection tube corresponding to the downstream tube wall 206 of the protection tube 250 and the second flow redirector 236 may be mounted on the inner surface of the protection tube corresponding to the upstream tube wall 208 of the protection tube 250. Herein, the first flow redirector 234 is positioned proximate to the inlet 210 of the PM sensor 201, and the second flow redirector is positioned proximate to the outlet 214 of the PM sensor 201. Thus, the first flow redirector 234 is closer to the inlet 210 than the second flow redirector 236 and the second flow redirector 236 is closer to the outlet 214 than the first flow redirector 234. The sensing portion of the PM sensor element 254 (e.g., the electrodes 220) may be inserted into the protection tube 250 such that the sensing portion of the sensor element 254 is closer to the second flow redirector than the first flow redirector. Furthermore, the PM sensor element 254 is closer to the outlet 214 than the inlet 210.

One end of the second flow redirector 236 may be attached to the inner surface of the upstream tube wall 208 of the protection tube 250, while the opposite end of the second flow redirector 236 may be unattached to the wall of the protection tube 250. For example, the opposite, unattached end of the second flow redirector is spaced away from and not in contact with the inner wall of the protection tube 250. Herein, the unattached end of the second flow redirector 236 may be closer to the outlet 214 of the PM sensor 201 than the inlet 210 and positioned a distance away from the unattached end of the first flow redirector 234. Furthermore, the sensing portion of the PM sensor element 254 may be closer to the unattached end of the second flow redirector 236, further separated from each of the attached end of the second flow redirector 236 and the inner surface of the downstream tube wall 208. Further still, the sensing potion of the PM sensor element 254 may be separated at a distance from the unattached end of the second flow redirector 236, thereby forming a gap between the unattached end of second flow redirector and the sensing portion of the PM sensor element 254. Thus the unattached end of the second flow redirector 236 and the sensing portion of the PM sensor element 254 are each closer to one another than the first flow redirector 234 and also closer the outlet 214 than the inlet 210 of the PM sensor 201, for example. The second flow redirector 236 extends across a portion of the protection tube 250, however, the unattached end of the second flow redirector 236 is spaced away from the inner surface of the protection tube 250. It will be appreciated by someone skilled in the art in view of the present disclosure that a plurality of second flow redirectors may be positioned inside the PM sensor 201. In one example embodiment shown in FIG. 2C, a plurality of parallel flow redirectors (e.g., embodied as semi-circular flow plates) may be positioned proximate to the sensor element, each plate positioned parallel with all other plates, although different plate surface areas may be provided by the different plates. In another example embodiment, a plurality angled flow plates may be positioned proximate to the sensor element as shown in FIG. 2F.

Similarly, one end of the first flow redirector 234 may be attached to the inner surface of the downstream tube wall 206 of the protection tube 250, while the opposite end of the first flow redirector 234 may be unattached to the wall of the protection tube 250. For example, the opposite, unattached end of the first flow redirector is spaced away from and not in contact with the inner wall of the protection tube 250. Herein, the unattached end of the first flow redirector 234 may be closer to the inlet 210 of the PM sensor 201 than the outlet 214 and positioned a distance away from the unattached end of the second flow redirector 236. In some embodiments, the length of the flow redirectors 234 and 236, determined as the distance the flow redirectors extend into the hollow space inside the protection tube 250 along the X-axis, may be equal. In other embodiments, the lengths of the flow redirectors 234 and 236 may be unequal, wherein one of the flow redirectors (first/second) may extend longer into the hollow space of the protection tube than the other flow redirector (second/first).

Further, the unattached ends of each of the first and second flow redirectors 234 and 236 form openings for exhaust gas flow to pass. As shown in FIGS. 2A-2B, the first opening formed between the unattached end of the first flow redirector 234 and the second opening formed between the unattached end of the second flow redirector 236 are on opposite sides of the protection tube 250 relative to the central axis. Further, the first flow redirector 234 extends from the inner wall of the protection tube 250 in a first direction and the second flow redirector 236 extends from the inner wall of the protection tube 250 in a second direction, opposite the first direction.

The first flow redirector 234 is separated from the second flow redirector 236 by a space/distance. The PM sensor element 254 is positioned between the first flow redirector 234 and the second flow redirector 236 such that the sensing portion of the PM sensor element extends into the space between the first flow redirector 234 and the second flow redirector 236. Herein, the sensing portion of the PM sensor element 254 is directed towards a direction opposite to the incoming exhaust flow 246, for example. The electrodes 220 of the PM sensor element 254 are facing towards the incoming exhaust flow 246 (towards the upstream tube wall 208, for example).

Typically, PM sensors suffer from issues of PM sensor sensitivity dependence on the exhaust flow rate through the passage in which the sensor is coupled whereby the PM sensor sensitivity increases when exhaust flow rate is higher than a threshold, and subsequently decreases when the exhaust flow rate is lower than the threshold. It may be possible to adjust the opening of the PM sensor as described below to increase or decrease the PM sensor opening based on when the exhaust flow rate is higher or lower than a threshold, thereby reducing the sensitivity dependence on the exhaust flow rate.

The protection tube 250 also includes a flow controller 238 positioned proximate to one or more of the inlet 210 and the first flow redirector 234. A size of the inlet opening into an interior of the PM sensor 201 is controlled by the position of the flow controller with respect to the first flow redirector, for example. As such, the size of the inlet opening (or the amount of opening of the inlet) of the PM sensor 201 controls an amount of exhaust air flow through the inlet 210 and into the interior of the PM sensor. When the amount of opening of the inlet is increased, then more exhaust gas flows into the PM sensor, and when the amount of opening of the inlet of the PM sensor is decreased, exhaust gas flow into the PM sensor is restricted. The increasing and the decreasing of the PM sensor inlet opening may be enabled by moving and/or rotating the flow controller 238 as described below. As such, the increasing and decreasing of the inlet opening results in a more consistent rate of exhaust flow to the sensing element 254. As a result, the sensitivity of the PM sensor may be maintained at a more consistent level and the sensor dependency on flow rate may be decreased. In this way, the PM sensor sensitivity dependence on the exhaust flow rate may be reduced.

As shown in FIGS. 2A-2B, the flow controller 238 is a movable plate coupled to the upstream tube wall 208 of the protection tube 250 via a hinge 240 at one end of the movable plate, and is further unattached or uncoupled to any additional structure at the opposite end of the movable plate. In alternate embodiments, the flow controller 238 may be a flapper valve or another type of adjustable element adapted to adjust an amount of opening of the inlet 210.

The unattached end of the movable plate is proximate to the unattached end of the first flow redirector 234. A distance separating the unattached end of the first flow redirector 234 and the unattached end of the movable plate of the flow controller 238 creates a gap, or an inlet opening 248, between the flow controller 238 and the first flow redirector 234. When the flow controller 238 is moved closer to the first flow redirector 234, thereby decreasing the distance separating the unattached end of the first flow redirector 234 and the unattached end of the movable plate of the flow controller 238, the inlet opening 248 is decreased. When the flow controller 238 is moved in the opposite direction, away from the first flow redirector 234, the inlet opening 248 of the PM sensor is increased. The hinge 240 connecting one end of the flow controller 238 to the wall of the protection tube 250 is positioned on the upstream side of the PM sensor 201, and coupled to the upstream tube wall 208 of the protection tube 250. The flow controller 238 is pivoted to rotate about an axis of the hinge 240. As shown in FIGS. 2A-2B, the hinge 240 is actuated by a motor actuator 256 and the motor actuator 256 may be an electric motor actuator, for example. In alternate embodiments, the actuator for actuating the flow controller 238 may be an alternate type of actuator in electronic communication with the controller.

In some embodiments, the first flow redirector 234 may be attached to the upstream tube wall 208, the second flow redirector may be attached to the downstream tube wall 206 and the flow controller may be attached to the downstream tube wall 206. In such an embodiment, the PM sensor element 254 may face on the same direction as the arrow indicated for incoming exhaust flow 246. In some example embodiments, a plurality of flow redirectors may be positioned along the inner surface of the protection tube to guide the particulates towards the PM sensor element 254 as shown in FIGS. 2C and 2F.

Controller 12 may send signals for adjusting the flow controller position to motor actuator 256. These signals may include commands to rotate the flow controller towards and away from the first flow redirector 234. For example, when the exhaust flow rate is higher than a threshold rate, the controller 12 may send signals to the motor actuator 256, which in turn actuates the hinge, thereby rotating the flow controller 238 in a first direction that decreases the inlet opening (as shown by the position of the flow controller 238 and smaller inlet opening 248 in FIG. 2B, as discussed further below). As an example, controller 12 may send signals to the motor actuator 256 to rotate the flow controller 30° in the anti-clockwise direction about the X-axis, when the exhaust flow rate is higher than the threshold. As such, the degree of opening may depend on the exhaust flow rate. However, when the exhaust flow rate falls below the threshold, then the controller may send signals to the motor actuator 256, to rotate the flow controller in a second direction, thereby increasing the inlet opening (as shown by the larger inlet opening 248 in FIG. 2A). As such, the second direction may be opposite to the first direction and rotating the flow controller may involve actuating the hinge thereby moving the flow controller in the second direction. As an example, controller 12 may command the motor actuator 256 to rotate the flow controller 30° in the clockwise direction about the X-axis when the exhaust flow rate falls below the threshold. In this way, the inlet opening 248 of the PM sensor 201 may be increased or decreased depending on whether the exhaust flow rate is lower or higher than the threshold by active adjustments made to the position of the flow controller 238. Additionally or alternatively, the controller 12 may adjust the position of the flow controller 238 as a function of the exhaust flow rate. Thus, as the exhaust flow rate increases, the controller 12 may rotate the flow controller 238 closer to the first flow redirector 234, thereby decreasing the inlet opening 248. In this way, the flow controller 238 may be adjusted into a plurality of positions based on the exhaust flow rate.

As an example, while operating the PM sensor to accumulate soot particulates, the controller 12 may send a control signal to an electric circuit to apply a voltage to the sensor electrodes of the PM sensor to trap the charged particulates onto the surface of the sensor electrodes. As another example, during PM sensor regeneration, the controller 12 may send a control signal to a regeneration circuit to close a switch in the regeneration circuit for a threshold time to apply a voltage to heating elements coupled to the sensor electrodes to heat the sensor electrodes. In this way, the sensor electrodes are heated to burn off soot particles deposited on the surface of the sensor electrodes. Example routines are described herein with reference to FIGS. 3-5.

In some embodiments, the flow controller 238 may be passively adjusted based on the pressure exerted on an outer face of the movable plate of the flow controller 238 by the incoming exhaust gas. Herein, the flow controller 238 may be coupled to the inside surface of the upstream tube wall 208 via a spring hinge capable of axial rotation. When the exhaust flow rate is higher than the threshold, the pressure exerted by the incoming exhaust gas on the flow controller may be higher, and that would cause the spring hinge to rotate in a first direction (for example anti-clockwise direction), thereby moving the flow controller 238 closer to the first flow redirector 234 and decreasing the inlet opening 248. In this embodiment, the degree or the amount by which the flow controller 238 rotates or moves may depend on the spring constant of the spring hinge, and the pressure exerted by the incoming exhaust gas. However, when the exhaust flow rate falls below a threshold, the pressure exerted by the incoming exhaust gas on the flow controller may be lower causing the spring hinge to rotate in a second direction, opposite to the first direction (for example, in clockwise direction), thereby moving the flow controller 238 away from the first flow director and increasing the inlet opening 248. Again, the degree or the amount by which the flow controller 238 rotates or moves may depend on the spring constant of the spring hinge, and the pressure exerted by the incoming exhaust gas. In some examples, when the exhaust flow rate is lower than the threshold, the spring hinge may in its equilibrium position, thereby the inlet opening may be maximally opened. In this example, the flow controller moves passively and is not controlled by the controller.

By moving the flow controller position based on the exhaust flow rate, it may be possible to adjust the inlet opening of the PM sensor so that the amount of exhaust gas entering the PM sensor and thus the rate at which particulates get deposited on the PM sensor element 254 is near constant (e.g., maintained at a relatively constant level). As such, the flow controller may be moved actively by actuating the motor actuator 256, or passively by the pressure exerted on the flow controller by the incoming exhaust flow. Regardless of whether the flow controller adjustment is active or passive, the rate of deposition of particulates on the PM sensor element is independent of the exhaust flow rate, thereby making the PM sensor sensitivity independent of the incoming exhaust flow rate. This is elucidated further with respect to the exhaust flow paths inside the PM sensor 201.

Incoming exhaust flow 246 (also called incoming exhaust or incoming exhaust gas) refers to exhaust upstream of the PM sensor 201, which enters the inlet 210 of the PM sensor 201. As such, the exhaust flow 246 is the exhaust gas that exits the DPF, for example. Due to the presence of the flow controller 238 proximate to the inlet 210 of the PM sensor 201, a portion of the incoming exhaust flow 246 gets blocked, and only a remaining portion of the incoming exhaust flow 246, indicated as exhaust flow 247 flows into the PM sensor inlet opening 248. The exhaust flow 247 flowing into the inlet opening 248 flows into the PM sensor inlet opening 248 via the space between the unattached end of the flow controller 238 and the downstream tube wall 206, for example. The exhaust flow 247 may include a portion of the incoming exhaust flow 246. Based on the flow rate of the incoming exhaust 246, the flow controller 238 may be rotated either actively via motor actuator 256 or passively via spring hinge, as described earlier. When the exhaust flow rate of the incoming exhaust 246 is lower than the threshold, then the flow controller 238 may be adjusted to increase the inlet opening 248 as shown in view 200 of FIG. 2A. As such, the adjustment of the flow controller 238 includes moving the flow controller 238 in a first (e.g., clockwise) direction away from the first flow redirector 234, thereby increasing the inlet opening 248. The exhaust flow 247 enters the PM sensor 201 through the inlet opening 248. The first flow redirector 234 then traps a first set of particulates in the exhaust flow 247 at the bottom surface of the first flow redirector 234 that faces the inlet 210 of the PM sensor 201. The first set of particulates include particulates in the exhaust flow 247 that are larger than a threshold size. The larger particulates and/or water droplets 242 that get trapped at the first flow redirector 234 may thus exit the PM sensor 201 via inlet 210, thereby reducing the amount of larger particulates depositing on the PM sensor element 254. In this way, the PM sensor element may be protected from impingement of water droplets and larger particulates and the PM sensor may be made more reliable.

The first flow redirector 234 further guides a portion of the exhaust flow (249) from the inlet opening 248 to one or more of the second flow redirector 236 and the PM sensor element 254. The exhaust flow 249 may include a portion of the incoming exhaust flow 246 (and a portion of exhaust flow 247) that is guided towards the PM sensor element 254 of the PM sensor 201 by the first flow redirector 234. For example, the first flow redirector 234 may guide a second set of particulates 244 in the exhaust flow 249 towards the PM sensor element 254, where they are subsequently deposited. As such, the second set of particulates 244 may be smaller in size compared to the first set of particulates 242 that were previously blocked at the first flow redirector 234, for example.

When the exhaust flow rate of the incoming exhaust 246 is higher than the threshold, then the flow controller 238 may be adjusted to decrease the inlet opening 248, as shown in view 260 of FIG. 2B. As such, the adjustment of the flow controller 238 includes moving the flow controller 238 in a second (e.g., anti-clockwise) direction towards the first flow redirector 234, thereby decreasing the inlet opening 248. The exhaust flow 247 enters the PM sensor 201 through a restricted inlet opening 248 (FIG. 2B). As explained with regard to FIG. 2A, the first flow redirector 234 traps a first set of particulates in the exhaust flow 247 at the bottom surface of the first flow redirector 234 that faces the inlet 210 of the PM sensor 201. Since the inlet opening is decreased, the amount of exhaust gas 249 entering the PM sensor inlet opening 248 is reduced.

The first flow redirector 234 further guides a portion of the exhaust flow 249 from the inlet opening 248 to one or more of the second flow redirector 236 and the PM sensor element 254 (see FIGS. 2A and 2B). The exhaust flow 249 refers to a portion of the incoming exhaust flow 246 (and also a portion of exhaust flow 247) that is guided towards the PM sensor element 254 of the PM sensor 201 by the first flow redirector 234. As such, the exhaust flow 249 flowing through a larger opening 248 in FIG. 2A may be larger than the exhaust flow 249 flowing through the restricted opening 248 in FIG. 2B. However in both views 200 and 260, the first flow redirector 234 may guide a second set of particulates 244 towards the PM sensor element 254, where they are subsequently deposited. The second flow redirector 236 positioned at a level higher than the sensing portion of the PM sensor element 254 further guides the second set of particulates 244 towards the PM sensor element 254. The second flow redirector 236 may further guide the exhaust flow to the sensing element 254 before it escapes out of the PM sensor 201. As such, the second set of particulates 244 may be smaller in size compared to the first set of particulates 242 that were previously blocked at the first flow redirector 234, for example. However by adjusting the inlet opening of the PM sensor, the amount of exhaust gas entering the PM sensor may be adjusted in order for the particulate deposition rate on the PM sensor element 254 to be remain constant. When the second set of particulates 244 are deposited on the PM sensor element 254, particularly on the electrodes 220 on the sensor substrate 216, the resistance as measured in the electric circuit 258 by the measurement device 226 decreases. The controller 12 may compute a soot load on the PM sensor electrodes 220 based on the resistance measured by the measurement device (such as measurement device 226 of FIGS. 2A and 2B, for example). When the soot load reaches a threshold load, the PM sensor electrodes 220 may be regenerated to clean the electrode surface off any particulates deposited on them. By monitoring the deposition rate and/or the time to regeneration of the PM sensor, it may be possible to diagnose leaks in the particulate filter located upstream of the PM sensor. As such, the second flow redirector 236 further guides a portion of the exhaust flow 251 through the outlet 214 of the PM sensor 201. Thus, exhaust flow 251 may be a portion of the incoming exhaust 246 that exits the PM sensor electrode via the outlet 214.

Thus, the exhaust flow to a PM sensor element positioned inside the PM sensor, where the PM sensor is positioned in an exhaust flow passage, may be increased responsive to an exhaust flow rate of exhaust flow in the exhaust flow passage being lower than a threshold. The exhaust flow to the PM sensor may further be decreased responsive to the exhaust flow rate being higher than the threshold. Increasing the exhaust flow includes rotating a flow controller located proximate to an inlet opening of the PM sensor in a first direction and furthermore decreasing the exhaust flow includes rotating the flow rate controller in a second direction, opposite the first direction. Rotating the flow controller in the first direction further includes moving the flow rate controller away from a first flow plate or first flow redirector positioned at or near the inlet opening of the PM sensor, and rotating the flow controller in the second direction further includes moving the flow rate controller towards the first flow plate of the PM sensor assembly. In one example, the rotation of the flow controller may be controlled by a controller and a motor actuator which may be actuated by the controller to rotate the hinge coupled to the flow controller. In other examples, the flow controller rotation may occur passively, without any signals from the controller. Herein, the pressure exerted by the incoming exhaust may rotate the flow controller coupled to the PM sensor via spring hinges, for example. The PM sensor may further include a second flow plate or second flow redirector located proximate to an outlet of the PM sensor, and the second flow plate may be separated from the first flow plate by a distance. The function of the first flow redirector may include one or more of trapping a first set of particulates in the exhaust flow at the inlet opening of the PM sensor, and guiding a second set of particulates in the exhaust flow from the inlet towards a PM sensor element positioned at or near the second flow plate to facilitate deposition of the second set of particulates onto the PM sensor element, the first set of particulates being larger than the second set of particulates. When a rate of deposition of the second set of particulates on the PM sensor element exceeds a threshold rate, a leak in a particulate filter located upstream of the PM sensor may be indicated. Herein, the first flow plate further guides the exhaust flow towards the second flow plate and wherein the second flow plate further redirects the exhaust flow towards the outlet of the PM sensor.

FIG. 2C shows a schematic view 265 of an example embodiment of the PM sensor 201. The second embodiment is substantially similar to the first embodiment described above with respect to FIGS. 2A and 2B. The PM sensor 201 may include the flow rate controller 238 that is adjusted based on exhaust flow rate inside the exhaust passage. For example, when the exhaust flow rate is higher than a threshold rate, the flow rate controller 238 is rotated towards the flow redirector 234, and thus reducing the inlet opening and reducing flow of exhaust PM into the PM sensor 201 through the inlet opening 248. Larger particulates and water droplets 242 are blocked by the flow redirector 234. However, instead of using a single second flow redirector (such as second flow redirector 236 shown in FIGS. 2A and 2B), it is possible to use a plurality of flow plates 266 as shown in FIG. 2C, to redirect the exhaust inside the PM sensor 201 towards the PM sensor element 254. Specifically, exhaust is distributed across the sensing electrodes 220 of the PM sensor element 254 with the help of the plurality of flow plates 266 as described below.

The plurality of flow plates 266 includes a series of parallel flow plates arranged along the upstream wall 208 extending to a length L inside the PM sensor protection tube 250. A first end of each of the plurality of flow plates 266 is coupled to an inner surface of the upstream wall 208, and a second, opposite end of each of the plurality of flow plates 266 is at a distance from the PM sensor element 254. Herein, each flow plate 268 of the plurality of flow plates 266 encloses an angle $\alpha$ with respect to the horizontal X-axis. In one example, the angle $\alpha$ may be 30°. In other examples, the angle $\alpha$ may be 45°. For example, the angle $\alpha$ may be within a range given by $0<\alpha<60°$, and $10<\alpha<50°$ in a more specific example. In an alternate example, the plurality of flow plates 266 may be positioned parallel to the X-axis, and hence parallel to the direction of exhaust flow (indicated by arrow 246) inside the exhaust passage 235.

In the example of FIG. 2C, each flow plate 268 of the plurality of flow plates 266 is parallel to one another, thus each flow plate is at an angle $\alpha$ with respect to the horizontal X-axis. In addition, each flow plate is separated by a space d from adjacent flow plates. Seven non-limiting examples of flow plates 268 are shown wherein each flow plate 268 is coupled to the inner surface of the upstream wall 208. Each flow plate 268 may include an open region (or opening) 270 juxtaposed to a closed region 272. Herein, the size of each of the open region 270 and the closed region 272 may vary across adjacent flow plates 268 as shown in FIGS. 2D and 2E.

Figure 2D:
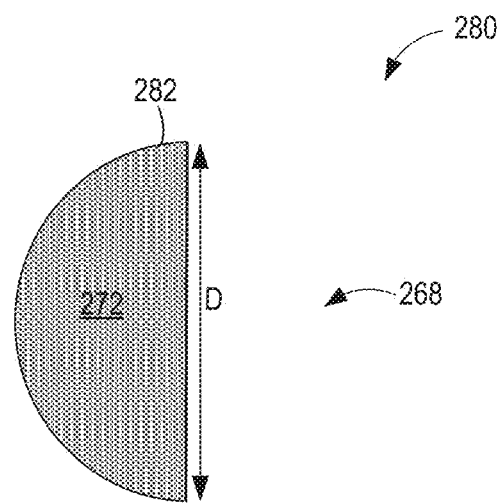
FIGS. 2D-2E show cross-sectional views of two example flow plates of the plurality of flow plates.
Figure 2E:
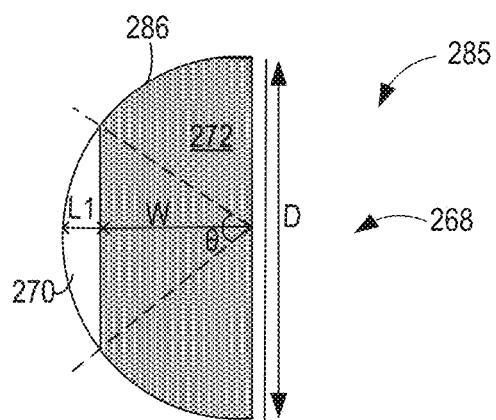
Figure 2F:
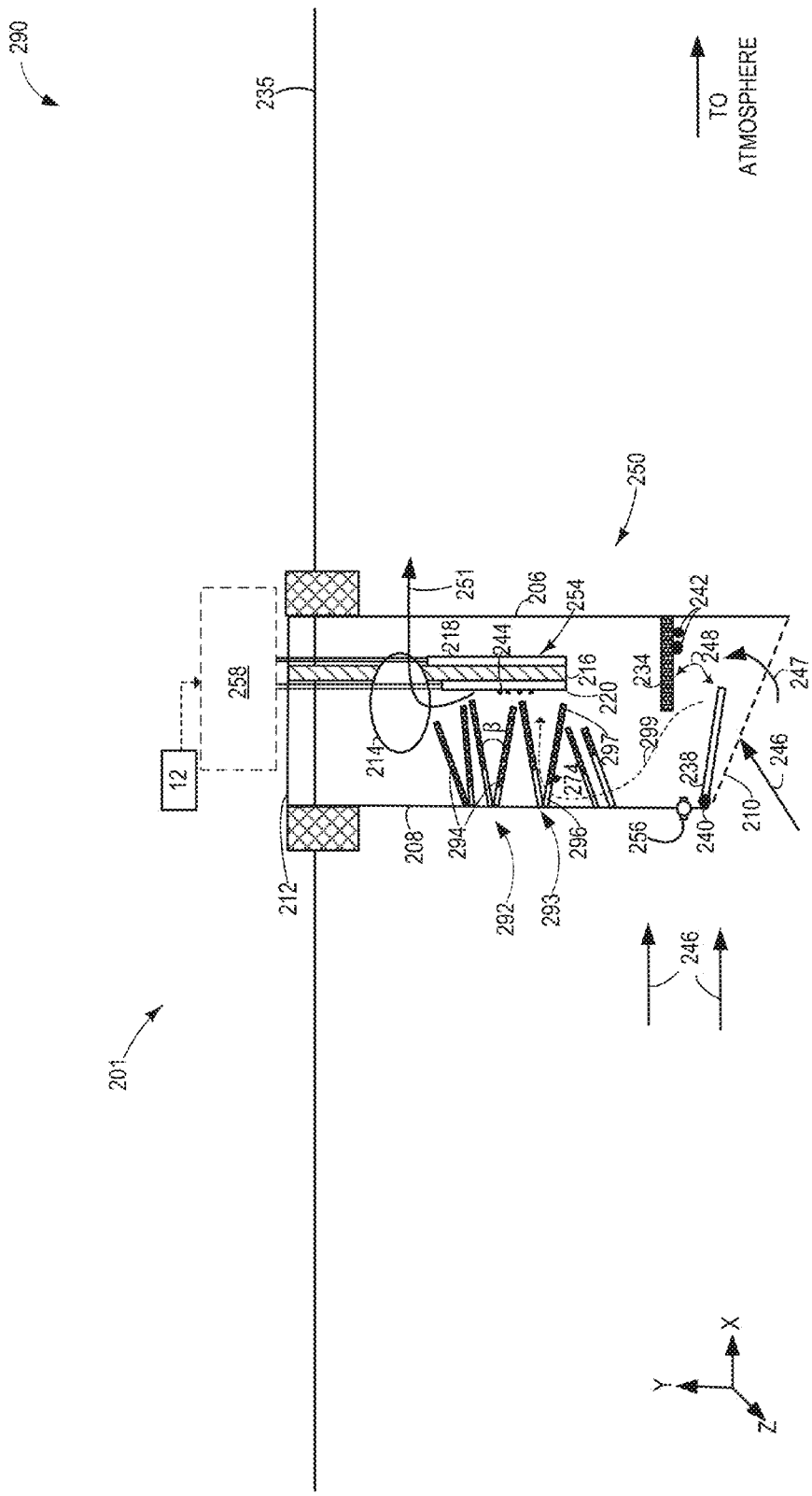
FIG. 2F shows an example embodiment of the PM sensor having a plurality of angled flow plates positioned proximate to the outlet of the PM sensor.

Turning to FIG. 2D, a cross-section view 280 of a top (the topmost plate, for example) flow plate of the plurality of flow plates 266 taken along an axis A-A' is shown. FIG. 2E shows a cross-section view 285 of a flow plate immediately below the topmost plate taken along an axis B-B'. Herein, the axis A-A' is parallel to the axis B-B'; both of which are at an angle $\alpha$ with respect to the horizontal X-axis. The topmost flow plate includes a semi-circular disc 282 of diameter D. Herein, the semi-circular region 272 of the disc 282 is a closed region implying that exhaust may not be able to flow through the topmost plate of the plurality of flow plates 266. The curved portion of the disc 268 is coupled to the curved inner surface of the upstream wall 208. In some examples, the curvature of the disc 282 may be smaller than the curvature of the protection tube of the PM sensor 201. Similar to the disc 282 of FIG. 2D, the flow plate shown in FIG. 2D is a semi-circular disc 286 of diameter D. However, the disc 286 includes both an open region 270 and a closed region 272. Herein, the open region 270 may be a segment of sagitta or length L1. Thus, the width W of the closed region 272 may be given by (D/2−L1).

The topmost flow plate of the plurality of flow plates may be manufactured as a solid semi-circular disc 282 of diameter D. The successive flow plates may also be manufactured from solid semi-circular discs, however with sections cutout to allow exhaust to flow through towards the electrodes of the sensor element. For example, the flow plate immediately below the topmost flow plate may be manufactured as a solid disc of diameter D (similar to disc 282), but with a segment of length L1 hollowed out. Herein, the segment that is hollowed out forms the open region 270 of the flow plate. By starting from a solid disc of diameter D, it is possible to increase the area of the region that is hollowed out or removed from the solid disc to increase the size of the open region 270. This in turn will result in decreasing the area the closed region 272. In a similar way, if the area of the region that is hollowed out from the solid disc is decreased, this will decrease the size of the open region 270, and increase the size of the closed region 272. As an example, the solid disc 286 includes the open region 270 that is in the form of a segment. Mathematically, the segment that is hollowed out to form the open region or opening 270 may be given by equation (1):

$$A_o = \frac{D^2}{8}(\theta - \sin\theta) \quad (1)$$

where Ao is the area of the open region 270, D is the diameter of the semi-circular disc, and θ is the central angle in radian.

The sagitta (or height) L1 of the segment may be given by equation (2):

$$L1 = \frac{D}{2}\left(1 - \cos\frac{\theta}{2}\right) \quad (2)$$

The topmost plate of the plurality of flow plates 266 may include only closed region 272, and may not include an open region. The flow plate immediately below the topmost plate of the plurality of flow plates 266 may include an open region of area Ao as described by equation (1). Thus, the area of the closed region, Ac, may be obtained by subtracting the area of the open region from the area A of the solid disc of diameter D, and may be given by equation (3):

$$A_c = A - A_o = \frac{\pi D^2}{4} - \frac{D^2}{8}(\theta - \sin\theta) \quad (3)$$

Successive flow plates of the plurality of flow plates 266 may be manufactured by increasing the area of the open region Ac that is cut out from the solid disc. For example, the third plate from the topmost of the plurality of flow plates may have 2 Ac removed, and so on. As such, the last of the bottommost flow plate of the plurality of flow plates will have the largest open region 270, and the smallest closed region 272. In this way, successive flow plates of the plurality of flow plates 266 may be formed. It may be appreciated that the diameter D of each of the flow plate of the plurality of flow plates 266 may be the same for all the plates. As such, this ensures that the distance of a straight edge of each of the semi-circular disc may be equidistant from the PM sensor element 254. Herein, the flow plates are semi-circular discs. However, various geometry and shapes of the flow plates may be used without deviating from the scope of the invention. Example shape includes rectangular, square, triangular, and the like, Returning to FIG. 2C, each of the flow plates formed as described with reference to FIGS. 2D and 2E, may be coupled to the inner surface of the upstream wall 208 of the protection tube 250. Herein, the curved portion of the semi-circular flow plate may be coupled to the inner surface of the upstream wall 208 (e.g., same side to which the flow controller 238 is coupled), and the straight edge or portion of the semi-circular plate be point towards the inside of the PM sensor protection tube 250. Specifically, the straight edge of the semi-circular plate may be positioned closer to the PM sensor element 254, while the curved portion of the semi-circular plate may be further away from the PM sensor element 254. In the view 260, the plurality of flow plates 266 have rectangular cross-section, however it may be appreciated that each of the flow plate 268 of the plurality of flow plates 266 are semi-circular discs as described with reference to FIGS. 2D and 2E.

The plurality of flow plates 266 are formed by arranging a series of flow plates 268 between the top surface 212 and the inlet opening 248 of the PM sensor 201. Herein, the topmost flow plate of the plurality of flow plates 266 may be closer to the top surface 212, and the bottommost flow plate of the plurality of flow plates 266 may be closer to the inlet opening 248. As such, a distance between the topmost flow plate and the bottommost flow plate may be based on a length of the sensing portion (or a distance to which the interdigitated electrodes 220 extend on the surface of the PM sensor substrate 216). As a non-limiting example, seven flow plates 268 are arranged with a spacing d (or space d in between), across length or distance L2. In one example configuration where the thickness w of each of flow plates 268 is the same, the distance L2 may be approximately equal to 7*(d+w). The space d between adjacent flow plates 268 of the plurality of flow plates 266 may not include any components. The space d and the distance L1 may be adjusted based on a distance to which the interdigitated electrodes 220 extend on the substrate 216 of the PM sensor element 254.

As described previously, except for the topmost plate of the plurality of flow plates 266, all the other flow plates of the plurality of flow plates 266 include an open region 270 and a closed region 272. The first flow redirector 234 traps a first set of particulates in the exhaust flow 247. The first set of particulates includes particulates in the exhaust flow 247 that are larger than a threshold size. The larger particulates and/or water droplets 242 that get trapped at the first flow redirector 234 may thus exit the PM sensor 201 via inlet 210, thereby reducing the amount of larger particulates depositing on the PM sensor element 254. Additionally, a second set of particulates 274 (that are smaller than the first set of particulates) may be able to slip through the opening 248. However, the second set of particulates 274 may be blocked by the closed region 272 of the plurality of flow plates 266. In this way, the PM sensor element may be protected from impingement of water droplets and larger particulates and the PM sensor may be made more reliable.

Each flow plate 268 of the plurality of flow plates 266 may divide exhaust flowing into the protection tube 250 through the inlet opening 248 into a first portion and a second portion. The first portion of the exhaust may flow through the open region 270 of the flow plate into the space d between the adjacent flow plates as shown by arrow 276. The second portion of the exhaust may flow through the open region of a first flow plate towards the open region of an adjacent flow plate that is located immediately above the first flow plate, for example. As such, exhaust may be divided into the first portion and second portion at each of the flow plates of the plurality of flow plates 266. Thus, the plurality of flow plates 266 may divide the incoming exhaust into multiple flow paths or streams. For the example of seven flow plates, the incoming exhaust may be divided into six streams, all of which are directed towards the electrodes 220. Exhaust may not flow through the topmost flow plate since it does not have an open region. If there are n flow plates, the exhaust may be divided into (n−1) streams. As such, the first portion may include a third set of particulates.

Herein, the third set of particulates (e.g., soot particulates) may be smaller compared to each of the first and second set of particulates. The third set of particulates may be captured across electrodes 220 of the PM sensor element 254. In this way, the soot particulates in the exhaust may be distributed evenly across the sensor electrodes. Once the third set of particulates are deposited on the sensor electrodes, the exhaust flows out of the PM sensor 201 through the outlet 214 positioned proximate to the PM sensor element 254. The controller 12 may control the electric circuit as explained with reference to FIGS. 2A and 2B to sense the third set of particulates accumulated across the electrodes 220, and determine a soot load on the PM sensor 201 based on the current/resistance change measured across the electrodes. As such, a leak in the particulate filter upstream of the PM sensor may be indicated when a rate of deposition of the third set of particulates on the PM sensor element exceeds a threshold rate.

The plurality of flow plates 266 shown in FIG. 2C include parallel flow plates arranged with a uniform spacing between them. Another example embodiment of the plurality of flow plates is shown schematic view 290 of FIG. 2F. Herein, a plurality of flow plates 292 may be manufactured and positioned similarly to the plurality of flow plates 266 of FIG. 2C. However, the plurality of flow plates 292 may include flow plates 294 that are all not parallel to one another. In the view 290, eight non-limiting flow plates 294 are shown. Two of the bottom most plates are shown to be parallel to each other. However, the remaining six of the flow plates 294 are at an angle β with respect to one another. Various combination of angled and parallel flow plates 294 may be possible. In one example embodiment, half of the flow plates may be parallel, and the remaining half of the flow plates may be at an angle with respect to each other. In another embodiment, all of the flow plates may be angled. For the angled plates, the angle β may not be the same for different pairs of adjacent flow plates.

Similar to each flow plate 268 of FIG. 2C, each flow plate 294 of FIG. 2F includes an open region 296 and a closed region 297. A length of the closed region 297 and the open region 296 may be different for each of the flow plate 294. For a pair of flow plates 293, the bottom flow plate includes a smaller closed region 296 than the top flow plate. Likewise, the bottom flow plate of the pair of flow plates 293 includes a larger closed region 297, than the top plate of the pair of flow plates. In this way, the closed regions of the pair of flow plates 293 may include an overlap, that further aids in trapping the second set of particulates 274 at the bottom plate, and guides the exhaust though the open region 296 towards electrodes 220 of the PM sensor element 254. Each pair of flow plates of the plurality of flow plates 292 may be formed in a similar way with overlapping closed regions. Exhaust may thus be guided through the plurality of flow plates 292. Specifically, the third set of particulates may be guided towards the electrodes 220 (as indicated by arrow 299), where the third set of particulates in the exhaust may be distributed evenly across the sensor electrodes. Once the third set of particulates are deposited on the sensor electrodes, the exhaust flows out of the PM sensor 201 through the outlet 214 positioned proximate to the PM sensor element 254, as described previously with reference to FIGS. 2A-2C.

In this way, soot particulates may be distributed evenly across the electrodes of the PM sensor. The PM sensor 201 through the outlet 214 positioned proximate to the PM sensor element 254. The controller 12 may control the electric circuit as explained with reference to FIGS. 2A and 2B to sense the third set of particulates accumulated across the electrodes 220, and determine a soot load on the PM sensor 201 based on the current/resistance change measured across the electrodes. As such, a leak in the particulate filter upstream of the PM sensor may be indicated when a rate of deposition of the third set of particulates on the PM sensor element exceeds a threshold rate.

FIGS. 2A-2F show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example.

The controller may perform a method 300 described below with reference to FIG. 3 to adjust the PM sensor inlet opening based on the exhaust flow rate. Instructions for carrying out method 300 and the rest of the methods included herein may be executed by a controller (such as controller 12 shown in FIG. 1 and FIGS. 2A-2B) based on instructions stored on a memory of the controller and in conjunction with signals received from sensors of the engine system, such as the sensors described above with reference to FIGS. 1, 2A and 2B. The controller may employ engine actuators of the engine system to adjust engine operation, according to the methods described below.

Figure 3:
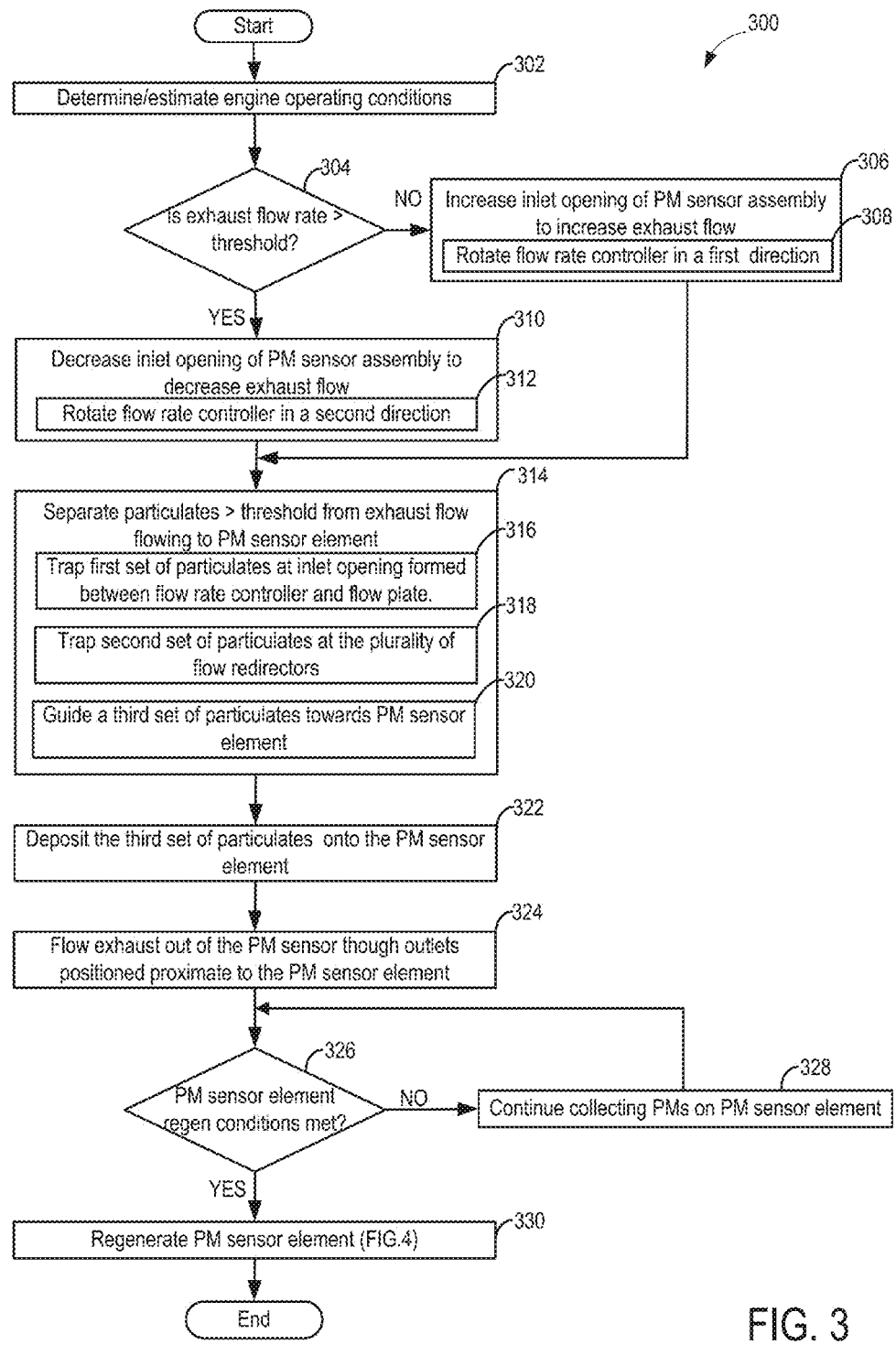
FIG. 3 shows a flow chart depicting a method for adjusting the inlet opening of the PM sensor based on the exhaust flow rate, and flowing exhaust through the plurality of flow plates towards a sensor element of the PM sensor.

Turning now to FIG. 3, a method 300 for adjusting the inlet opening of a PM sensor (such as a PM sensor 201 of FIGS. 1, 2A and 2B) based on an exhaust flow rate is described. Specifically, the amount of opening of the inlet to the PM sensor positioned in an exhaust flow may be increased or decreased when the exhaust flow rate of the exhaust flow upstream of the particulate matter sensor is respectively higher or lower than the threshold.

At 302, method 300 includes determining and/or estimating engine operating conditions. Engine operating conditions determined may include, for example, engine speed, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc.

The engine exhaust passage may include one or more sensors positioned upstream and/or downstream of the DPF for determining an exhaust flow rate. For example, the engine may include flow meters for exhaust mass flow measurements and determining exhaust flow rate at the inlet of the PM sensor. In some examples, the incoming exhaust flow rate at the inlet of the PM sensor may be determined based on an intake exhaust flow rate. Thus, in some examples, the exhaust gas flow rate through the exhaust passage in which the PM sensor is installed may be estimated base on alternate engine sensors and/or operating conditions.

At 304, the method includes determining whether the exhaust flow rate is higher than a threshold. In one example, the threshold may be a threshold rate based on a desired rate of deposition of the particulates on the particulate matter sensor element. In other examples, the threshold may be based on a time to regeneration threshold of the PM sensor. Typically, when the incoming exhaust flow rate is high, the time to reach regeneration threshold of the PM sensor is lower than when the exhaust flow rate is low.

If the exhaust flow rate is lower than the threshold, then method 300 proceeds to 306, where the amount of opening of the PM sensor inlet is increased. As discussed above with reference to FIGS. 2A-2B, the PM sensor may include a first flow redirector and a flow controller (such as flow controller 238 shown in FIGS. 2A-2B) positioned at the inlet, where an end of the flow controller is positioned a distance away from the first flow redirector to generate a gap at the inlet. As such, increasing the amount of opening comprises increasing the gap between the first flow redirector and the flow controller by rotating the flow controller in a first direction away from the first flow redirector at 308. Rotating the flow controller in the first direction includes sending signals to the motor actuator to rotate the hinge coupling the flow controller to the protection tube in a first direction for a threshold amount. In one example, the flow controller may be rotated 30° about a central axis of the PM sensor in an anti-clockwise. Increasing the gap between the flow controller and the first flow redirector allows more exhaust to flow into the PM sensor, thereby increasing the amount of particulates flowing into the PM sensor which in turn increased the rate of deposition of particulates on the PM sensor, for example. However, if the exhaust flow rate is higher than the threshold, then method 300 proceeds to 310 where the amount of opening of the inlet is decreased. As such, decreasing the amount of opening comprises decreasing the gap between the first flow redirector and the flow controller by rotating the flow controller in a second direction, opposite to the first direction, and away from the first flow redirector at 312. Rotating the flow controller in the second direction includes sending signals to the motor actuator to rotate the hinge coupling the flow controller to the protection tube in the second direction for a threshold amount. In one example, the flow controller may be rotated 30° about a central axis of the PM sensor in an anti-clockwise. Decreasing the gap between the flow controller and the first flow redirector restricts the exhaust flowing into the PM sensor, thereby decreasing the amount of particulates and thereby decreasing the rate of deposition of particulates on the PM sensor, for example.

In one example, the opening is increased (at 306) or decreased (at 310) by rotating the flow controller by a threshold amount, the threshold amount is a fixed amount which is further based on the exhaust flow rate. For example, when the exhaust flow rate is above the threshold, then the flow controller may be rotated by 30° in the second direction (at 312), however, if the exhaust is lower than the threshold, the flow rate controller may be rotated by 30° in the first direction (at 308). In other example, the flow rate controller may be rotated by a threshold amount, wherein the threshold amount is variable and further based on the exhaust flow rate. For example, at 312, if the exhaust flow rate is over the threshold by a certain amount, the amount of opening will be decreased by a greater amount as the amount by which the exhaust flow rate above the threshold increases. Similarly, at 308, if the exhaust flow rate is below the threshold by a certain amount, the amount of opening will be increased by a greater amount as the amount by which the exhaust flow rate below the threshold decreases. Said another way, the amount of opening may depend on the amount by which the exhaust flow rate differs from the threshold.

Once the inlet opening is adjusted based on the exhaust flow rate (either increased at 306 or decreased at 310), method 300 proceeds to 314. At 314, particulates traveling in the exhaust flow may be separated based on size from the exhaust flow flowing to the PM sensor sensing element. A first set of particulates (e.g., larger particulates and/or water droplets) may be trapped at a first flow redirector (such as first flow redirector 234 shown in FIGS. 2A-2B), for example, thereby allowing only a second and third set of particulates in the exhaust to enter (e.g., pass through) the PM sensor inlet opening. Herein, the first set of particulates may be larger than each of the second and the third set of particulates. The second set of particulates may be blocked at the plurality of flow redirectors at 318. In one example, the plurality of flow redirectors or flow plates may include parallel flow plates that are coupled to an inside surface of an upstream wall of the PM sensor (such as upstream wall 208 of FIGS. 2A-2C and 2F). In another example, the plurality of flow plates may include one or more of angled and parallel flow plates. In both examples, each flow plate may include an open region and a closed region. Exhaust may flow through the open region towards a space between adjacent flow plates. Additionally, the second set of particulates may be blocked at the closed region. The third set of particulates may be guided through the open region into the space between flow pates and then towards the PM sensor element. The third set of particulates including smaller soot particulates may then be directed towards the PM sensor element at 320 (as described in FIGS. 2C and 2F), and subsequently deposited on the PM sensor element (e.g., sensor element 254 shown in FIGS. 2C-2F) at 322. Next at 324, the method includes flowing the exhaust out of the PM sensor through outlets positioned proximate to the PM sensor element. In one example configuration, two circular shaped outlets may be formed on two opposite surfaces of the PM sensor and may be positioned closer to the PM sensor element than the inlet opening. Exhaust may flow upwards (against gravity) to flow towards the outlet from the PM sensor element, and then flow out of the PM sensor through the outlets.

Next at 326, the method includes determining if PM sensor regeneration conditions are met. Specifically, when the PM load on the PM sensor element is greater than a threshold, or when a resistance of the PM sensor drops to a threshold resistance, the PM sensor regeneration conditions may be considered met, and the PM sensor may need to be regenerated to enable further PM detection. If the PM sensor regeneration conditions are met, then method 300 proceeds to 330 where the PM sensor may be regenerated as described in method 400 of FIG. 4. However, if PM sensor regeneration conditions are not met when checked at 326, then method 300 proceeds to 328, where the PM sensor continues to collect PMs on the PM sensor. As such, any PMs not deposited on the PM sensor is directed out of the PM sensor via the outlet of the PM sensor.

Method 300 described above may be performed by a controller to maintain the PM sensor deposition rate by adjusting the inlet opening of the PM sensor. In other embodiments, where the PM sensor includes a spring hinge to couple the flow controller to the protection tube of the PM sensor, the adjusting of the PM sensor inlet opening may be achieved passively without an intervention by the controller. Herein, based on the pressure exerted by the incoming exhaust gas, the spring hinge may rotate the flow controller, and thereby control the amount of opening at the inlet of the PM sensor.

Thus, an example method includes adjusting an amount of opening of an inlet to a particulate matter sensor positioned in an exhaust flow in response to an exhaust flow rate of the exhaust flow upstream of the particulate matter sensor, and flowing exhaust past a plurality of flow plates towards a particulate matter sensor element positioned proximate to the plurality of flow plates. The adjusting includes increasing the amount of opening of the inlet when the exhaust flow rate falls below a threshold rate and further includes decreasing the amount of opening of the inlet when the exhaust flow rate exceeds the threshold rate. The particulate matter sensor includes a flow redirector and a flow controller positioned at the inlet, where the flow controller and the flow redirector are coupled to different, opposite surfaces of the PM sensor such that a gap is formed between the flow controller and the flow redirector at the inlet. Increasing the amount of opening includes increasing the gap between the flow redirector and the flow controller by rotating the flow controller in a first direction away from the flow redirector and decreasing the amount of opening comprises decreasing the gap between the flow redirector and the flow controller by rotating the flow controller in a second direction, opposite the first direction, towards the flow redirector. The plurality of flow plates further includes one or more of parallel plates and angled plates separated from one another by a space and positioned proximate to an outlet of the particulate matter sensor, the plurality of flow plates separated from the flow redirector by a distance. The plurality of flow plates directs exhaust gases coming through the gap formed at the inlet between the flow controller and the flow redirector, into the space formed between the plurality of flow plates towards the particulate matter sensor element positioned proximate to the outlet of the particulate matter sensor.

Thus, an example method for a particulate matter (PM) sensor, includes increasing exhaust flow to a PM sensor element positioned inside the PM sensor, where the PM sensor is positioned in an exhaust flow passage, responsive to an exhaust flow rate of exhaust flow in the exhaust flow passage being lower than a threshold, decreasing the exhaust flow to the PM sensor element responsive to the exhaust flow rate being higher than the threshold, and flowing the exhaust in-between a plurality of flow redirectors towards the PM sensor element positioned proximate to the plurality of flow redirectors. Additionally or alternatively, the increasing exhaust flow may include rotating a flow rate controller located proximate to an inlet opening of the PM sensor in a first direction and wherein the decreasing the exhaust flow includes rotating the flow rate controller in a second direction, opposite the first direction. Additionally or alternatively, the rotating the flow controller in the first direction further may include moving the flow rate controller away from a flow plate positioned at or near the inlet opening of the PM sensor, and wherein the rotating the flow controller in the second direction further may include moving the flow rate controller towards the flow plate of the PM sensor assembly. Additionally or alternatively, the plurality of flow redirectors may be separated from each other by a space, and wherein each of the plurality of flow redirectors includes a plate with an opening that allows a first portion of the exhaust to flow from the gap into the space between the plurality of flow directors towards the sensor element, and a second portion of the exhaust to flow towards the opening of an adjacent flow redirector, the opening of adjacent flow directors being different in size. Additionally or alternatively, the plurality of flow redirectors may be parallel to each other and wherein the space between adjacent flow redirectors may be uniform. Additionally or alternatively, the plurality of flow redirectors may be angled plates and wherein the space between adjacent flow redirectors may be non-uniform. Additionally or alternatively, the method may include trapping a first set of particulates in the exhaust flow at the inlet opening of the PM sensor, trapping a second set of particulates at the plurality of flow redirectors, the second set of particulates being smaller than the first set of particulates, guiding a third set of particulates in the exhaust flow from the space between adjacent flow redirectors towards a PM sensor element positioned at or near the plurality of flow redirectors to facilitate deposition of the third set of particulates onto the PM sensor element, the third set of particulates being smaller than each of the first set of particulates and the second set of particulates, and indicating a leak in a particulate filter located upstream of the PM sensor when a rate of deposition of the third set of particulates on the PM sensor element exceeds a threshold rate.

Figure 4:
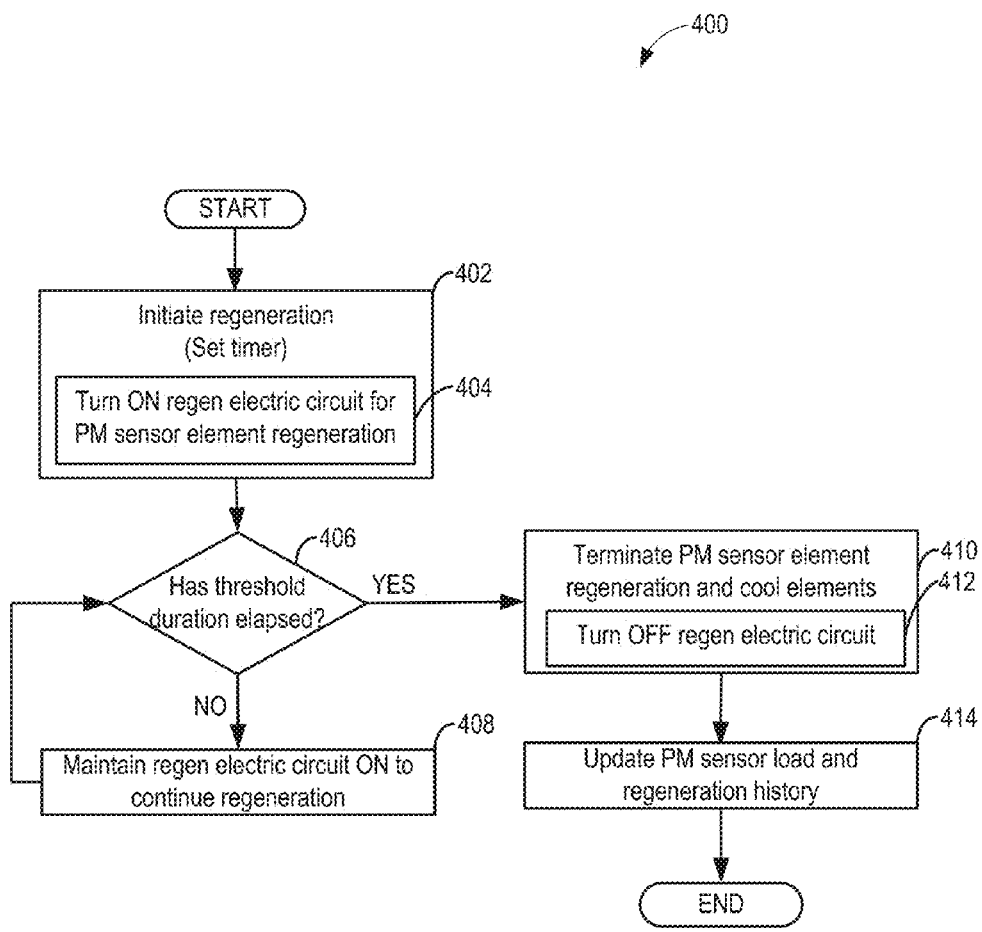
FIG. 4 shows a chart depicting a method for performing regeneration of the PM sensor.

Turning now to FIG. 4, a method 400 for regenerating the PM sensor (such as a PM sensor 106 shown at FIG. 1, and/or PM sensor 201 of FIGS. 2A-F, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may require regeneration to enable further PM detection. At 402, regeneration of the PM sensor may be initiated and the PM sensor may be regenerated by heating up the sensor at 404. The PM sensor may be heated by actuating a heating element until the soot load of the sensor has been sufficiently reduced by oxidation of the carbon particles between the electrodes. The PM sensor regeneration is typically controlled by using timers and the timer may be set for a threshold duration at 402. Alternatively, the sensor regeneration may be controlled using a temperature measurement of the sensor tip, or by the control of power to the heater, or any or all of these. When a timer is used for PM sensor regeneration, then method 400 includes checking if the threshold duration has elapsed at 406. If the threshold duration has not elapsed (e.g., "NO" at 406), then method 400 proceeds to 408 where the regeneration circuit may be kept ON to continue regeneration and the method ends. If threshold duration has elapsed (e.g., "YES" at 406), then method 400 proceeds to 410 where the PM sensor regeneration may be terminated and the electric circuit may be turned off at 412. Further, the sensor electrodes may be cooled to the exhaust temperature for example. Method 400 proceeds to 414 where the PM sensor load and regeneration history may be updated and stored in memory. For example, a frequency of PM sensor regeneration and/or an average duration between sensor regenerations may be updated and the method ends.

The engine exhaust passage may include one or more PM sensors positioned upstream and/or downstream of the DPF for determining a soot load of the DPF. When the PM sensor is positioned upstream of the DPF, based on the resistance change following soot deposited on the plurality of electrodes of the PM sensor, a soot load on the sensor may be inferred. The soot load thus determined, may be used to update the soot load on the DPF, for example. If the soot load on the DPF is greater than a threshold for DPF regeneration, then the controller may adjust engine-operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF.

Figure 5:
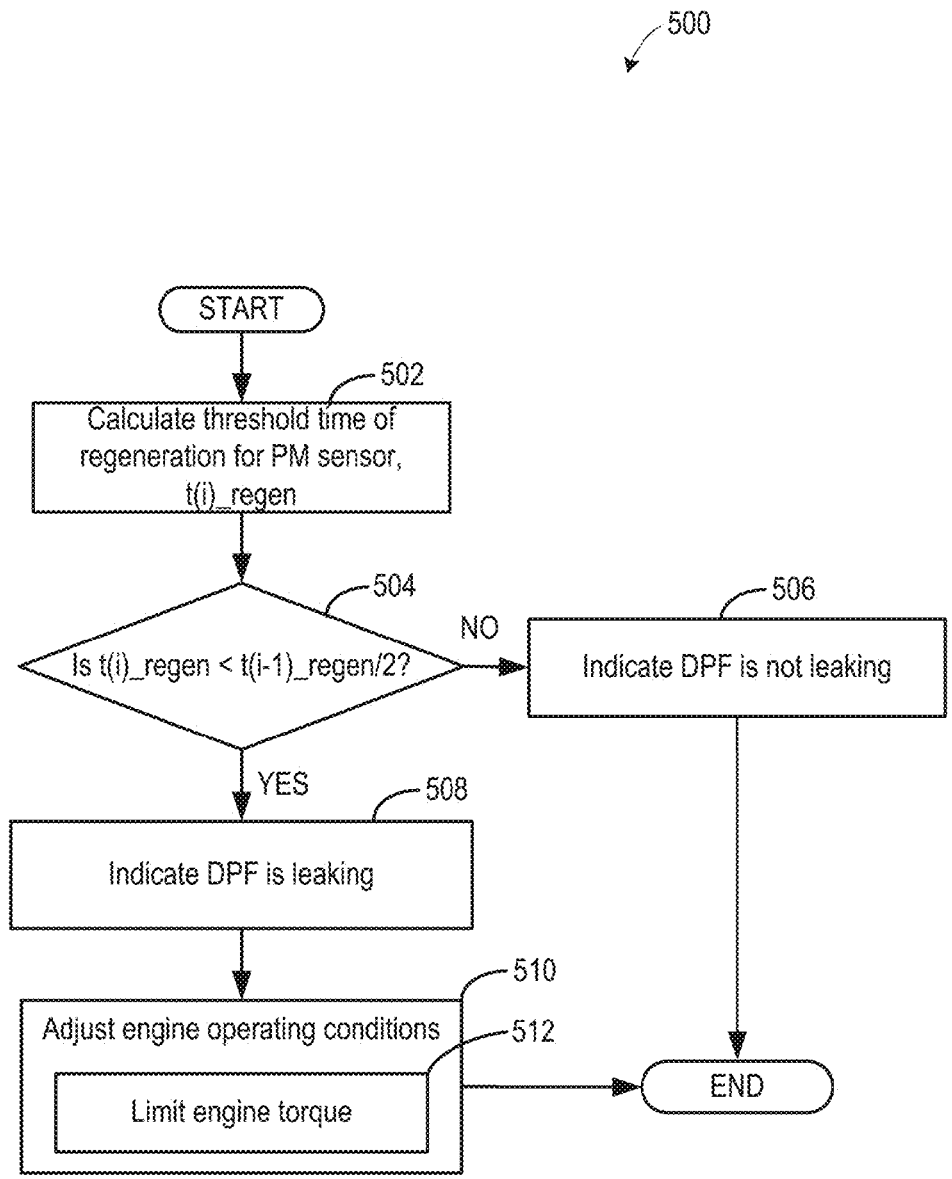
FIG. 5 shows a flow chart depicting a method for diagnosing leaks in a particulate filter positioned upstream of the PM sensor.

Turning now to FIG. 5, an example method 500 for diagnosing DPF function based on the regeneration time of the PM sensor is shown. At 502, it may be calculated by the controller, through calibration, the time of regeneration for the PM sensor, t(i)_regen, which is the time measured from end of previous regeneration to the start of current regeneration of the PM sensor. At 504, compare t(i)_regen to t(i−1)_regen, which is the previously calibrated time of regeneration of the PM sensor. From this, it may be inferred that the soot sensor may cycle through regeneration multiple times in order to diagnose the DPF. If the t(i)_regen is less than half the value of t(i−1) region, then at 508 indicate DPF is leaking, and DPF degradation signal is initiated. Alternatively, or additionally to the process mentioned above, the DPF may be diagnosed using other parameters, such as exhaust temperature, engine speed/load, rate of deposition of particulates onto the sensor electrodes, etc. In one example, if the rate of deposition of the soot particulates on the sensor electrodes exceeds a threshold rate, then a leak in the DPF may be indicated. The degradation signal may be initiated by, for example, a malfunction indication light on diagnostic code. In addition, method 500 includes adjusting engine operation based on indicating leak in the DPF at 510. Adjusting engine operation may include limiting engine torque at 512, for example. In one example, responsive to detecting leak in the DPF, engine power and torque may be reduced. Reducing the engine power and torque may reduce the amount of PM emissions in the exhaust. For example, adjusting engine operation may include reducing fuel injected in a diesel engine under heavy load conditions thereby reducing torque. Additionally or alternatively, responsive to detecting leak in the DPF, an EGR usage may be decreased. Additionally or alternatively, an engine warning sign will appear on the dashboard to indicate the maximal distance vehicle can drive before DPF service check.

A current regeneration time of less than half of the previous regeneration time may indicate that the time for electric circuit to reach the R_regen threshold is significantly shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change in regeneration time of the soot sensor does not reach threshold t_regen, then at 506 DPF leaking is not indicated. In this way, leaks in a particulate filter positioned upstream of the particulate matter sensor may be detected based on a rate of deposition of the particulates on the particulate matter sensor electrodes.

Figure 6:
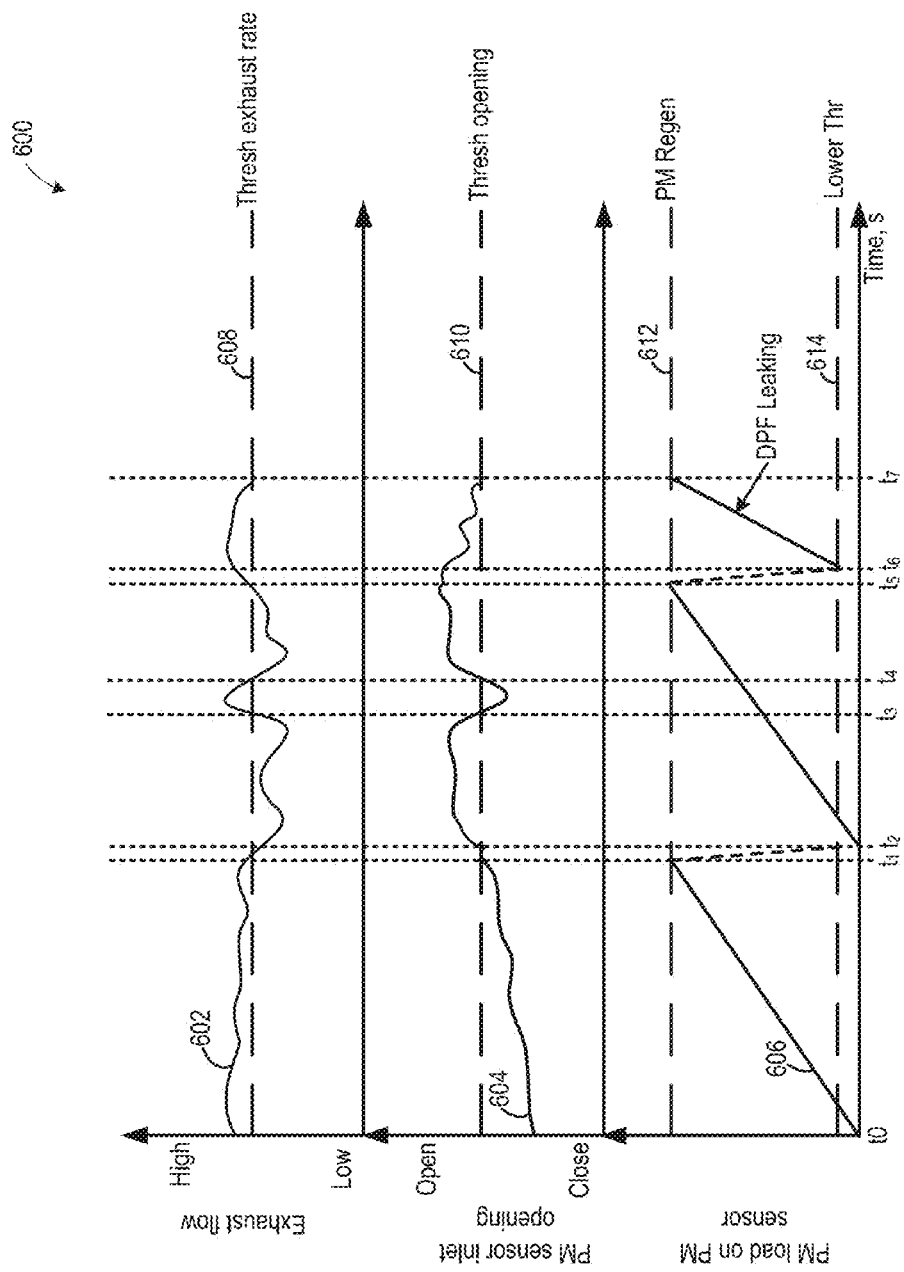
FIG. 6 shows an example relationship between the inlet opening of the PM sensor and a PM sensor loading based on the exhaust flow rate.

Turning now to FIG. 6, map 600 shows an example relationship between an exhaust flow rate, a PM sensor inlet opening, and a PM load on a PM sensor. The first plot 602 of 600 shows the exhaust flow rate as determined by a flow rate sensor positioned upstream of the PM sensor. The second plot 604 shows the PM sensor inlet opening as determined by rotating a flow controller positioned proximate to an inlet of the PM sensor as described in FIGS. 2A and 2B. The third plot 606 shows the PM load on the PM sensor. The dashed line 612 indicates the PM regeneration threshold, while dashed line 614 indicates the Lower_Thr, indicating that the PM sensor electrodes are clean, as described in FIG. 4. Dashed lines 608 and 610 indicate threshold exhaust rate and threshold inlet opening respectively. For each plot, time is depicted along the x (horizontal) axis while values of each respective parameter are depicted along the y (vertical) axis.

At time t0, the PM sensor is relatively clean (plot 606) with low PM load lower than Lower_Thr (line 614) indicating that the PM sensor has been regenerated recently. The exhaust flow rate (plot 602) is higher than the threshold exhaust rate (line 608). When the exhaust rate is higher than the threshold, the PM sensor inlet opening may be adjusted by adjusting a movable plate (such as flow controller 238 in FIGS. 2A and 2B) to a final position between a first (closed) position and a second (open) position. As such, the final position may be closer to the first position than the second position. Herein, the movable plate may be adjusted by actuating a motor to rotate a hinge coupling the movable plate to the PM sensor in a first direction (anti-clockwise, for example) towards a first flow redirector proximate to an inlet of the PM sensor. The technical effect of adjusting the PM sensor inlet opening to the final position closer to the first close position, is that the gap between the movable plate and the first flow redirector is decreased, thereby decreasing the amount of PMs entering the PM sensor and subsequently deposited on the PM sensor electrode. In this way, the PM sensor deposition rate may be maintained at a desired level. Herein, the slope of the line 606 indicates the rate of deposition of PMs on the PM sensor electrode.

Between t0 and t1, the exhaust flow (plot 602) continues to remain higher than the threshold exhaust rate (line 608), as a result, the PM sensor inlet opening is maintained closer to the first closed position. During the time between t0 and t1, the PM sensor continues to collect particulates at a constant rate indicated by line 606.

At t1, the PM load on the PM sensor reaches the threshold for regeneration (dashed line 612). During the time between t1 and t2, PM sensor may be regenerated. A controller may have instructions to send a regeneration signal to a regeneration circuit, responsive to the PM level data. Regenerating the PM sensor includes operating the regeneration portion of the electric circuit for a threshold time and/or threshold duration as described in FIG. 4 to burn off the PMs deposited between the electrodes of the PM sensor, for example.

At t2, the PM sensor is relatively clean indicated by low PM load (plot 606). However, the exhaust flow rate (plot 602) falls below the threshold rate (line 608) at time t2. Between t2 and t3, when the exhaust rate is lower than the threshold, the PM sensor inlet opening may be adjusted by adjusting a movable plate (such as flow controller 238 in FIGS. 2A and 2B) to a final position closer to the second position than the first position (plot 604). Herein, the movable plate may be adjusted by actuating a motor to rotate a hinge coupling the movable plate to the PM sensor in a second direction (clockwise, for example) away from the first flow redirector proximate to the inlet of the PM sensor. The technical effect of adjusting the PM sensor inlet opening to the final position closer to the second open position, is that the gap between the movable plate and the first flow redirector is increased, thereby increasing the amount of PMs entering the PM sensor and subsequently deposited on the PM sensor electrode. In this way, the PM sensor deposition rate may be maintained at the desired level indicated by the slope of line 606. As such the slope of the line 606 between t2 and t4 is similar to the slope of the line 606 between t0 and t1. In this way, by adjusting the inlet opening based on the exhaust flow rate, the PM sensor loading may be maintained at a constant rate.

Between t3 and t4, the exhaust flow rate (plot 602) rises about the threshold rate (line 608). By adjusting the PM sensor inlet opening to a final position closer to a first close position as explained earlier, the PM sensor loading is maintained at the desired rate (slope of line 606). In a similar way, when the exhaust flow rises about the threshold between t4 and t5, the PM sensor inlet opening is adjusted to a final position closer to the second open position. By actively adjusting the inlet opening based on the exhaust flow rate, the PM sensor loading may be maintained at the desired level. In this way, the PM sensor sensitivity may become independent of the exhaust flow rate.

Again at t5, the PM load (plot 606) reaches the regeneration threshold (dashed line 612). Hence between t5 and t6, the PM sensor may be regenerated as explained earlier. At t6, the PM sensor is relatively clean. Furthermore, the PM sensor inlet opening is adjusted to a final position closer to the second open position as the exhaust flow (plot 602) remains higher than the threshold (line 608). However, irrespective of actively adjusting the PM sensor inlet opening, the PM load on the PM sensor (plot 606) increases sharply, indicating that the rate of deposition of particulates on the PM sensor is higher than the desired deposition rate, indicating that the DPF located upstream of the PM sensor is leaking. Thus, in response to a current rate of deposition of particulates on the PM sensor rising above a desired rate of deposition of particulates on the PM sensor, DPF leaks may be determined and a diagnostic code may be set. For example, an MIL may be set indicating that the DPF needs to be replaced. By virtue of the PM sensor being independent of the exhaust rate, DPF leakage may be detected in a timely manner, thereby reducing the possibility of operating the engine with a leaking particulate filter and thus reducing soot particle emission in the exhaust.

In this way, by adjusting the inlet opening based on the exhaust flow rate, the PM sensor loading may be maintained at a constant rate and the dependence of PM sensor sensitivity on exhaust flow rate may be further reduced. Thus, the technical effect of increasing the PM sensor inlet opening when the exhaust flow rate falls below the threshold and decreasing the opening when the exhaust flow rate rises above the threshold is that the rate of deposition of particulates on the PM sensor electrodes remain near constant. The PM sensor sensitivity is independent of the incoming exhaust flow rate, thereby measuring PMs exiting the DPF more accurately and reliably. Thus, any leaks or degradation of the DPF may be detected more efficiently and effectively.

The systems and methods described above also provide for a method of particulate matter sensing, in an exhaust system, the method comprising adjusting an amount of opening of an inlet to a particulate matter sensor positioned in an exhaust flow in response to an exhaust flow rate of the exhaust flow upstream of the particulate matter sensor and flowing exhaust past a plurality of flow plates towards a particulate matter sensor element positioned proximate to the plurality of flow plates. In a first example of the method, the method may additionally or alternatively include wherein the adjusting includes increasing the amount of opening of the inlet when the exhaust flow rate falls below a threshold rate and further includes decreasing the amount of opening of the inlet when the exhaust flow rate exceeds the threshold rate. A second example of the method optionally includes the first example, and further includes wherein the particulate matter sensor includes a flow redirector and a flow controller positioned at the inlet, where the flow controller and the flow redirector are coupled to different, opposite surfaces of the PM sensor such that a gap is formed between the flow controller and the flow redirector at the inlet. A third example of the method optionally includes one or more of the first and the second examples, and further includes wherein the increasing the amount of opening comprises increasing the gap between the flow redirector and the flow controller by rotating the flow controller in a first direction away from the flow redirector. A fourth example of the method optionally includes one or more of the first through the third examples, and further includes wherein the decreasing the amount of opening comprises decreasing the gap between the flow redirector and the flow controller by rotating the flow controller in a second direction, opposite the first direction, towards the flow redirector. A fifth example of the method optionally includes one or more of the first through the fourth examples, and further includes wherein the plurality of flow plates comprises one or more of parallel plates and angled plates separated from one another by a space and positioned proximate to an outlet of the particulate matter sensor, the plurality of flow plates separated from the flow redirector by a distance. A sixth example of the method optionally includes one or more of the first through the fifth examples, and further comprises directing exhaust gases through the gap formed at the inlet between the flow controller and the flow redirector, into the space formed between the plurality of flow plates towards the particulate matter sensor element positioned proximate to the outlet of the particulate matter sensor. A seventh example of the method optionally includes one or more of the first through the sixth examples, and further including detecting leaks in a particulate filter positioned upstream of the particulate matter sensor and indicating degradation of the particulate filter based on a rate of deposition of the particulates on the particulate matter sensor element. An eighth example of the method optionally includes one or more of the first through the seventh examples, and further wherein the threshold rate is based on a desired rate of deposition of the particulates on the particulate matter sensor element.

The systems and methods described above also provide for a method of particulate matter sensing, in a particulate matter sensor system, the method comprising increasing exhaust flow to a PM sensor element positioned inside the PM sensor, where the PM sensor is positioned in an exhaust flow passage, responsive to an exhaust flow rate of exhaust flow in the exhaust flow passage being lower than a threshold and decreasing the exhaust flow to the PM sensor element responsive to the exhaust flow rate being higher than the threshold. In a first example of the method, the method may additionally or alternatively include wherein the increasing exhaust flow includes rotating a flow rate controller located proximate to an inlet opening of the PM sensor in a first direction and wherein the decreasing the exhaust flow includes rotating the flow rate controller in a second direction, opposite the first direction, and flowing the exhaust in-between a plurality of flow redirectors towards the PM sensor element positioned proximate to the plurality of flow redirectors. A second example of the method optionally includes the first example, and further includes wherein the rotating the flow controller in the first direction further includes moving the flow rate controller away from a flow plate positioned at or near the inlet opening of the PM sensor, and wherein the rotating the flow controller in the second direction further includes moving the flow rate controller towards the flow plate of the PM sensor assembly. A third example of the method optionally includes one or more of the first and the second examples, and further includes wherein the plurality of flow redirectors are separated from each other by a space, and wherein each of the plurality of flow redirectors includes a plate with an opening that allows a first portion of the exhaust to flow from the opening into the space between the plurality of flow directors towards the sensor element, and a second portion of the exhaust to flow towards the opening of an adjacent flow redirector, the opening of adjacent flow directors being different in size. A fourth example of the method optionally includes one or more of the first through the third examples, and further includes wherein the plurality of flow redirectors is parallel to each other and wherein the space between adjacent flow redirectors is uniform. A fifth example of the method optionally includes one or more of the first through the fourth examples, and further includes wherein the plurality of flow redirectors are angled plates and wherein the space between adjacent flow redirectors is non-uniform. A sixth example of the method optionally includes one or more of the first through the fifth examples, and further includes trapping a first set of particulates in the exhaust flow at the inlet opening of the PM sensor, trapping a second set of particulates at the plurality of flow redirectors, the second set of particulates being smaller than the first set of particulates; and guiding a third set of particulates in the exhaust flow from the space between adjacent flow redirectors towards a PM sensor element positioned at or near the plurality of flow redirectors to facilitate deposition of the third set of particulates onto the PM sensor element, the third set of particulates being smaller than each of the first set of particulates and the second set of particulates, and indicating a leak in a particulate filter located upstream of the PM sensor when a rate of deposition of the third set of particulates on the PM sensor element exceeds a threshold rate.

In another representation, the method optionally includes one or more of the first through the sixth examples, and further includes wherein the flow plate further guides the exhaust flow towards the plurality flow redirectors and wherein the plurality of flow plate further redirects the exhaust flow towards the outlet of the PM sensor.

The systems and methods described above also provide for a particulate matter sensor comprising a first flow redirector proximate to an inlet of the PM sensor, a plurality of second flow redirectors, the plurality of second flow redirectors separated from the first flow redirector by a distance, a PM sensor element, where at least a portion of the PM sensor element is positioned between a topmost flow redirector and a bottommost flow redirector of the plurality of second flow redirectors, and a movable plate positioned at or near the inlet of the PM sensor adapted to adjust an inlet opening of the inlet. In a first example of the particulate matter sensor, the sensor may additionally or alternatively include a controller with computer-readable instructions stored on non-transitory memory for adjusting the movable plate into a final position at or between a first position having a smaller amount of inlet opening and a second position having a larger amount of inlet opening based on an exhaust flow rate of exhaust gas upstream of the PM sensor. A second example of the particulate matter sensor optionally includes the first example and further wherein adjusting the movable plate into the final position includes adjusting the movable plate closer to the first position than the second position as the exhaust flow rate increases and further includes adjusting the flow controller closer to the second position than the first position as the exhaust flow rate decreases. A third example of the particulate matter sensor optionally includes one or more of the first and the second examples, and further includes instructions for indicating a leak in a particulate filter located upstream of the PM sensor when a current rate of deposition of particulates on the PM sensor exceeds a desired rate of deposition of particulates on the PM sensor Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
adjusting an amount of opening of an inlet to a particulate matter sensor positioned in an exhaust flow in response to an exhaust flow rate of the exhaust flow upstream of the particulate matter sensor by rotating a flow controller of the particulate matter sensor; and
flowing exhaust past the flow controller of the particulate matter sensor, then past a plurality of flow plates of the particulate matter sensor, and then to a particulate matter sensor element of the particulate matter sensor, wherein the flow controller, the plurality of flow plates, and the particulate matter sensor element are all housed within a protective tube of the particulate matter sensor, and wherein the protective tube is positioned in an exhaust flow passage.

2. The method of claim 1, wherein the adjusting includes increasing the amount of opening of the inlet when the exhaust flow rate falls below a threshold exhaust flow rate and further includes decreasing the amount of opening of the inlet when the exhaust flow rate exceeds the threshold exhaust flow rate.

3. The method of claim 2, wherein the flow controller is positioned at the inlet, and wherein the particulate matter sensor includes a flow redirector at the inlet, the flow controller and the flow redirector coupled to different, opposite surfaces of the particulate matter sensor such that a gap is formed between the flow controller and the flow redirector at the inlet.

4. The method of claim 3, wherein the increasing the amount of opening comprises increasing the gap between the flow redirector and the flow controller by rotating the flow controller in a first direction away from the flow redirector.

5. The method of claim 4, wherein the decreasing the amount of opening comprises decreasing the gap between the flow redirector and the flow controller by rotating the flow controller in a second direction, opposite the first direction, towards the flow redirector.

6. The method of 3, wherein the plurality of flow plates comprises one or more of parallel plates and angled plates separated from one another by a space, the plurality of flow plates separated from the flow redirector by a distance.

7. The method of claim 6, wherein flowing the exhaust gas towards the particulate matter sensor element comprises directing exhaust gases through the gap formed at the inlet between the flow controller and the flow redirector, and into the space formed between the plurality of flow plates.

8. The method of claim 7, further including detecting leaks in a particulate filter positioned upstream of the particulate matter sensor and indicating degradation of the particulate filter based on a rate of deposition of particulates on the particulate matter sensor element.

9. The method of claim 8, wherein the threshold exhaust flow rate is based on a desired rate of deposition of the particulates on the particulate matter sensor element.

10. A method for a particulate matter (PM) sensor, comprising:
increasing exhaust flow to a PM sensor element of the PM sensor, the PM sensor element positioned inside a protective tube of the PM sensor, where the protective tube of the PM sensor is positioned in an exhaust flow passage, responsive to an exhaust flow rate of exhaust flow in the exhaust flow passage being lower than a threshold;
decreasing the exhaust flow to the PM sensor element responsive to the exhaust flow rate being higher than the threshold; and
flowing the exhaust in-between a plurality of flow redirectors of the PM sensor and towards the PM sensor element positioned downstream of the plurality of flow redirectors, wherein the plurality of flow redirectors is further positioned within the protective tube of the PM sensor, and wherein the protective tube defines an inlet of the PM sensor that opens into the exhaust flow passage in a direction substantially perpendicular to a direction of the exhaust flow.

11. The method of claim 10, wherein the increasing exhaust flow includes rotating a flow rate controller located at an inlet opening of the PM sensor in a first direction and wherein the decreasing the exhaust flow includes rotating the flow rate controller in a second direction, opposite the first direction.

12. The method of claim 11, wherein the rotating the flow rate controller in the first direction further includes moving the flow rate controller away from a flow plate of the PM sensor positioned at the inlet opening of the PM sensor, and wherein the rotating the flow rate controller in the second direction further includes moving the flow rate controller towards the flow plate positioned at the inlet of the PM sensor.

13. The method of claim 12, wherein the plurality of flow redirectors is separated from each other by a space, and wherein each of the plurality of flow redirectors includes a flat semi-circular plate with an opening that allows a first portion of the exhaust to flow from the opening into the space between the plurality of flow directors towards the PM sensor element, and a second portion of the exhaust to flow towards an opening of an adjacent flow redirector, the opening of adjacent flow redirectors of the plurality of flow redirectors being different in size.

14. The method of claim 13, wherein the plurality of flow redirectors is parallel to each other, and wherein the space between adjacent flow redirectors is uniform.

15. The method of claim 13, wherein the plurality of flow redirectors is angled plates, and wherein the space between adjacent flow redirectors is non-uniform.

16. The method of claim 13, further comprising:
trapping a first set of particulates in the exhaust flow at the inlet opening of the PM sensor;
trapping a second set of particulates at the plurality of flow redirectors, the second set of particulates being smaller than the first set of particulates;
guiding a third set of particulates in the exhaust flow from the space between adjacent flow redirectors towards the PM sensor element positioned at the plurality of flow redirectors to facilitate deposition of the third set of particulates onto the PM sensor element, the third set of particulates being smaller than each of the first set of particulates and the second set of particulates; and
indicating a leak in a particulate filter located upstream of the PM sensor when a rate of deposition of the third set of particulates on the PM sensor element exceeds a threshold rate.

17. A method for a particulate matter (PM) sensor, comprising:
increasing exhaust flow to a PM sensor element of the PM sensor, where the PM sensor is positioned in an exhaust flow passage, responsive to an exhaust flow rate of exhaust flow in the exhaust flow passage being lower than a threshold;
decreasing the exhaust flow to the PM sensor element responsive to the exhaust flow rate being higher than the threshold; and
flowing the exhaust in-between a plurality of flow redirectors towards the PM sensor element positioned downstream of the plurality of flow redirectors of the PM sensor,
wherein the increasing exhaust flow includes rotating a flow rate controller located at an inlet opening of the PM sensor in a first direction and wherein the decreasing the exhaust flow includes rotating the flow rate controller in a second direction, opposite the first direction,
wherein the rotating the flow rate controller in the first direction further includes moving the flow rate controller away from a flow plate of the PM sensor positioned at the inlet opening of the PM sensor, and wherein the rotating the flow rate controller in the second direction further includes moving the flow rate controller towards the flow plate positioned at the inlet of the PM sensor, and wherein the plurality of flow redirectors is separated from each other by a space, and wherein each of the plurality of flow redirectors includes a flat semi-circular plate with an opening that allows a first portion of the exhaust to flow from the opening into the space between the plurality of flow directors towards the PM sensor element, and a second portion of the exhaust to flow towards an opening of an adjacent flow redirector, the opening of adjacent flow redirectors of the plurality of flow redirectors being different in size.

* * * * *